US012702581B1

(12) United States Patent
Bishop

(10) Patent No.: US 12,702,581 B1
(45) Date of Patent: Aug. 11, 2026

(54) SENSOR FOR DETECTING THE FILL STATE OF A MEDICAL FLUID BAG

(71) Applicant: FILLSENSE LLC, Tiverton, RI (US)

(72) Inventor: Robert Bishop, Tiverton, RI (US)

(73) Assignee: FILLSENSE LLC, Tiverton, RI (US)

( * ) Notice: Subject to any disclaimer, the term of this patent is extended or adjusted under 35 U.S.C. 154(b) by 0 days.

(21) Appl. No.: 19/391,613

(22) Filed: Nov. 17, 2025

Related U.S. Application Data

(60) Provisional application No. 63/866,038, filed on Aug. 18, 2025.

(51) Int. Cl.
*A61F 5/445* (2006.01)
*A61F 5/44* (2006.01)
*A61M 5/14* (2006.01)

(52) U.S. Cl.
CPC ............ *A61F 5/445* (2013.01); *A61F 5/4404* (2013.01); *A61M 5/14* (2013.01); *A61M 2205/18* (2013.01)

(58) Field of Classification Search
CPC ......... A61F 5/445; A61F 5/4404; A61M 5/14; A61M 2205/18
USPC ...................................................... 604/93.01
See application file for complete search history.

(56) References Cited

U.S. PATENT DOCUMENTS

2014/0142485 A1* 5/2014 Berry ................. G08B 21/0446 602/19
2017/0140103 A1* 5/2017 Angelides ............. A61F 5/4404
2022/0192564 A1 6/2022 Kriscovich et al.

FOREIGN PATENT DOCUMENTS

AU 2021105360 10/2021
GB 2636256 A1 6/2025

* cited by examiner

*Primary Examiner* — Phillip A Gray
(74) *Attorney, Agent, or Firm* — VLP Law Group, LLP; David J. Thibodeau, Jr.

(57) ABSTRACT

A warning device for checking if an ostomy, drainage, or wound bag is full and needs to be emptied or if an IV bag dispensing medication or blood is empty and needs to be replaced. The warning device incorporates a unique sensor that adapts to the shape of the filled bag. The sensor can be easily attached to the outside of bags currently in commercial production or optionally integrated by a manufacturer onto a bag and the sensor does not require any additional countervailing force or external reference surface. An electronic module attached to the sensor can be programmed to produce a warning signal when an ostomy or drainage bag is full or when a bag dispensing medication or blood is below a predetermined level or is almost empty.

20 Claims, 30 Drawing Sheets

Urostomy Bag Filled To Above Level of Stretch Cord Sensor

Illustration Of An Ostomy Bag Showing Where
It Attaches To A Person

Urostomy Bag Front View Image
Simulating Person In A Vertical Standing Position

Urostomy Bag Side View Image
Simulating A Person In A Vertical Standing Position Or Leaning Back Urostomy Bag Side View Image
Simulating A Person Bending Forward Urostomy Bag Tilting Left
Simulating A Person Leaning To One Side Urostomy Bag Tilting Right
Simulating A Person Leaning To The Opposite Side Urostomy Bag
Simulating A Person In A Sitting Position Prior Art
From Davis
UK Patent Application GB 2636256

Prior Art
From Davis
UK Patent Application GB 2636256

Urostomy Bag
Simulating Person
Bending Forward

Limitations Of Rigid Davis Frame

Prior Art
From Kriscovich
Pub. No.:
US 2022/0192564 AI

Prior Art
From Kriscovich
Pub. No.: US 2022/0192564 AI

Prior Art
From Kriscovich
Pub. No.:
US 2022/0192564 AI

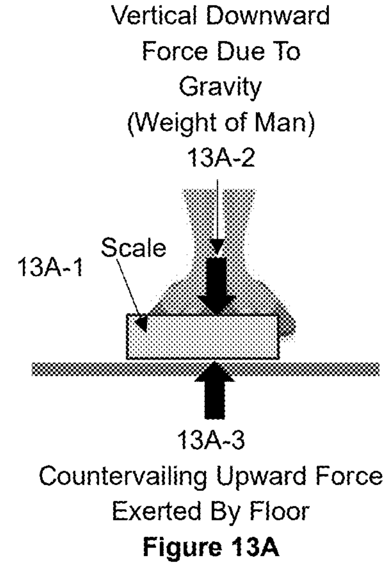
Figure 13A
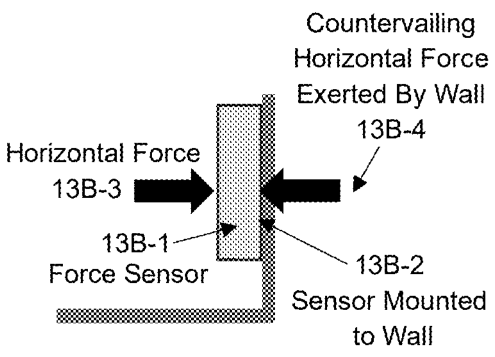
Figure 13B
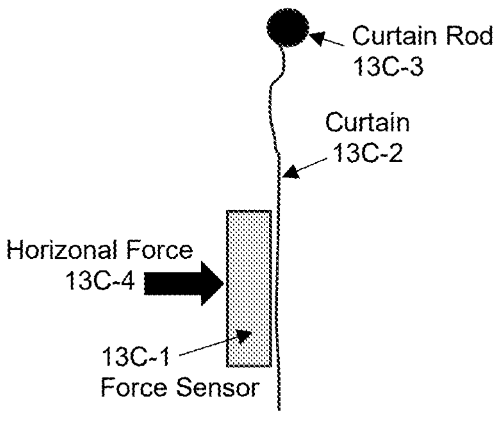
Figure 13C
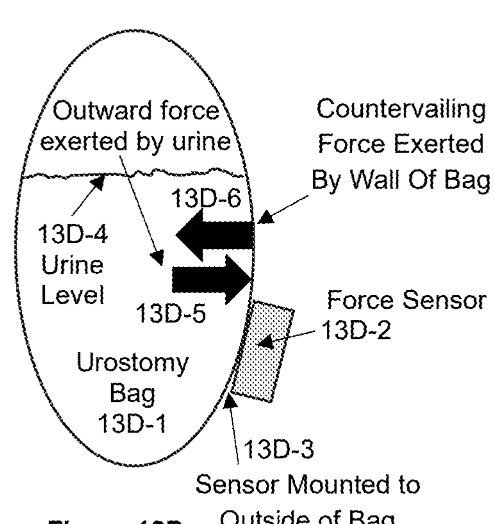
Figure 13D
How Countervailing Forces Work
Figure 13

Prior Art
From Stalmann Australian
Application AU 2021105360 A4

Hinge Sensor

Prior Art
From Stalmann Australian
Application AU 2021105360 A4

Capacitor Sensor

Prior Art
From Stalmann Australian
Application AU 2021105360 A4

Inductive Sensor

Prior Art
Body-Wrap With Pocket For Ostomy Bag

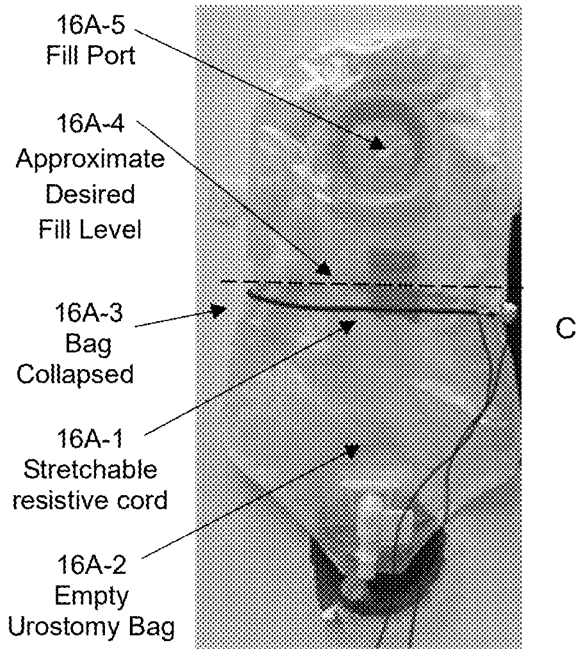

Empty Urostomy Bag Showing Resistive Stretch Cord Sensor Wrapped Around Bag

Figure 16A

Fill Port
16B-4
Resistive
Stretch
Cord
Sensor
16B-1
16B-3
Bag
Collapsed
16B-2
Empty
Urostomy
Bag Stretch Cord Sensor Is Made Smaller Than Perimeter Of Urostomy Bag Sides Of Flaccid Bag Collapsed To Fit Within Perimeter Of Stretch Cord Sensor When Sensor Is Unstretched

Figure 16B

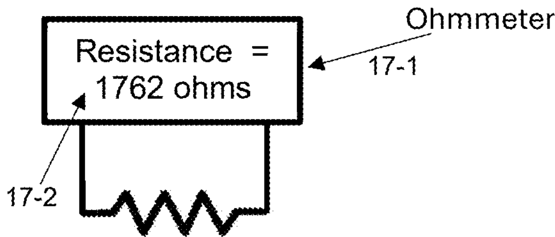

Resistance of stretch cord sensor measured by ohmmeter wrapped around empty bag shown in Figure 16A

Figure 17

Urostomy Bag Filling With Liquid

Resistance of stretch cord sensor corresponding to fill level shown in Figure 18

Illustration of Stretch Sensor Adapting To Shape of Bag And Producing A Countervailing Force Photograph Of Stretch Sensor Adapting To Shape Of Convatec Urostomy Bag Photograph Of Stretch Sensor Adapting To Shape Of Convatec Urostomy Bag Tilted To The Right Level of Liquid at Approximate Level of Stretchable Cord Sensor 22-1

Urostomy Bag Filled To Approximate Level of Stretch Cord Sensor

Resistance of Stretch Cord Sensor Corresponding To Fill Level Shown In Figure 22

Urostomy Bag Filled To Above Level of Stretch Cord Sensor

Resistance of Stretch Cord Sensor Corresponding To Fill Level Shown In Figure 24

Stretch Cord Sensor Adapts To Shape Of Urostomy Bag In Vertical Position 1

Stretch Cord Sensor Adapting To Shape In Vertical Position 1 When Bag Is Pushed In From Front Of Bag Stretch Cord Sensor Adapts To Shape Of Urostomy Bag In Position 2

Stretch Cord Sensor Adapting To Shape When Bag In Position 2 Is Squeezed On Side Of Bag Circuit Diagram For Warning Device

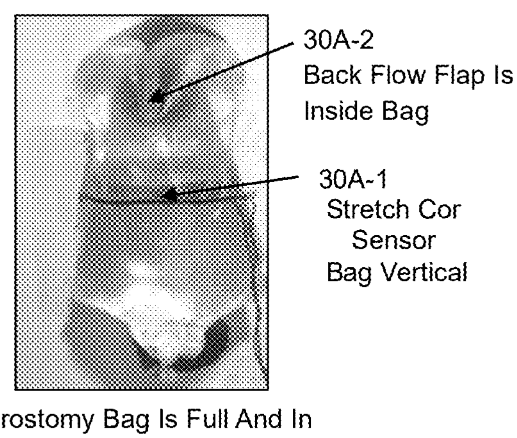

Urostomy Bag Is Full And In Vertical Position

Figure 30A

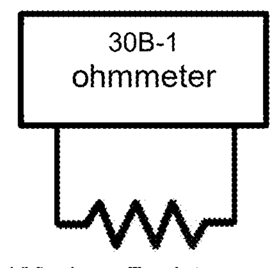

2166 ohms Resistance of Stretch Cord Sensor Corresponding To Fill Level and Vertical Position Of Ba Shown In Figure 30A

Figure 30B

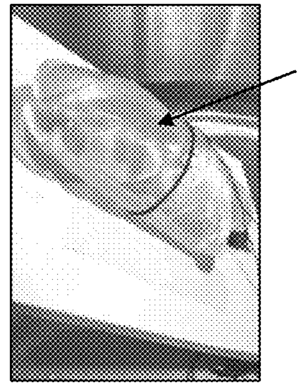

31A-1
Bag
Approximately
At 45 Degrees

Urostomy Bag Is Full And Tilted Approximately 45°

Figure 31A

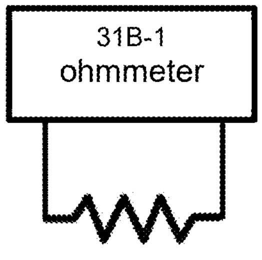

2207 ohms Resistance of Stretch Cord Sensor Corresponding To Fill Level and Tilt Angle Shown In Figure 31A

Figure 31B

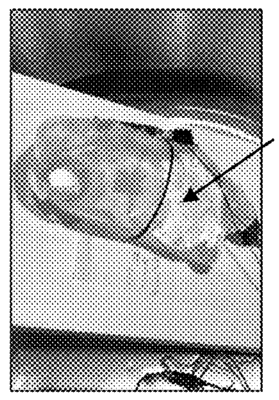

32A-1
Bag
Approximately
At 25 Degrees

Urostomy Bag Is Full And Tilted Approximately 25°

Figure 32A

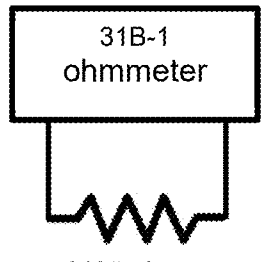

2197 ohms Resistance of Stretch Cord Sensor Corresponding To Fill Level and Tilt Angle Shown In Figure 32A

Figure 32B

Long Stretch Sensor

Short Stretch Sensor With Non-Stretch Cords

Sensor Module And Electronic Processing Module For Resistive Stretch Sensor

Sensor Module And Electronic Processing Module For Any Type Of Stretch Sensor

Graph From manufacturer's datasheet

Change In Capacitance Value
As A Function Of Extension For Alpha Part Number EC100-N-421-AO1

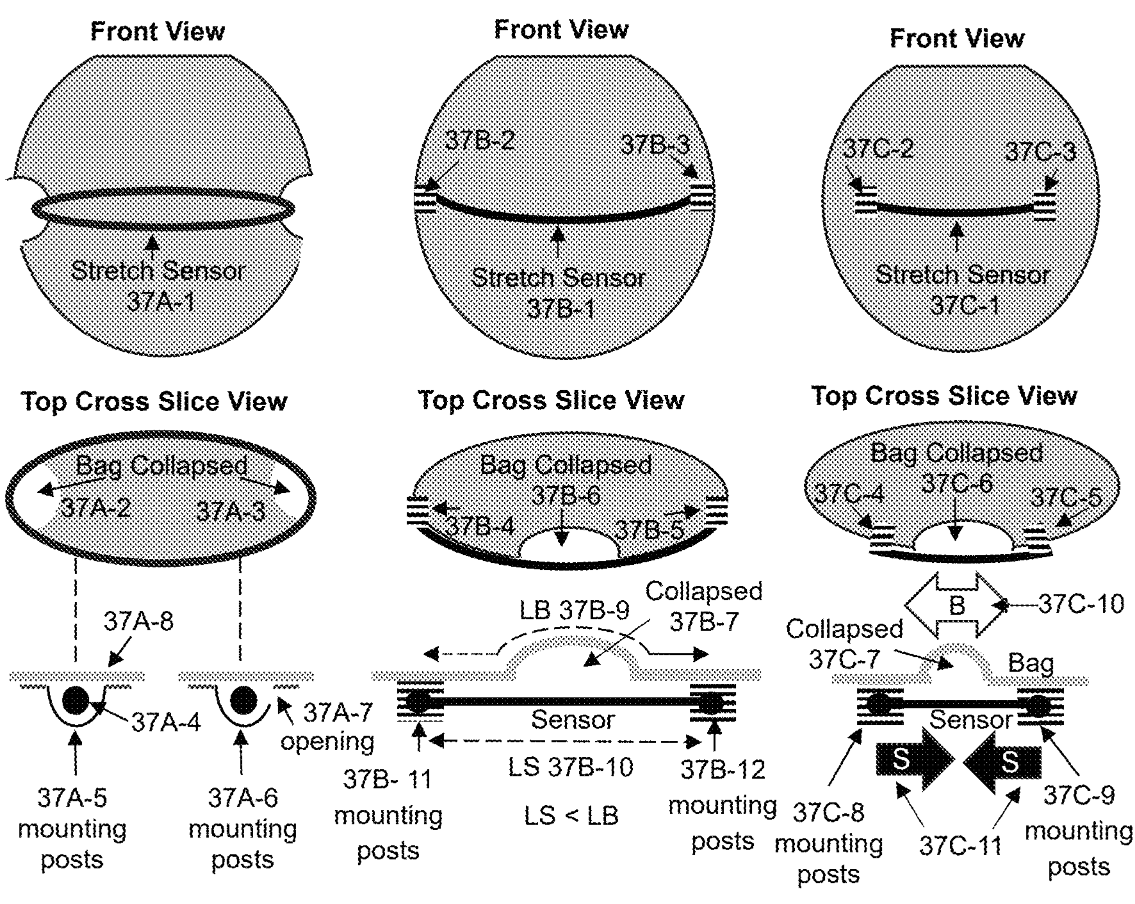
Figure 37A
Figure 37B
Figure 37C
Perimeter of bag at 37D-2 is greater than perimeter of sensor at 37D-1 when the bag is empty and the sensor not stretched
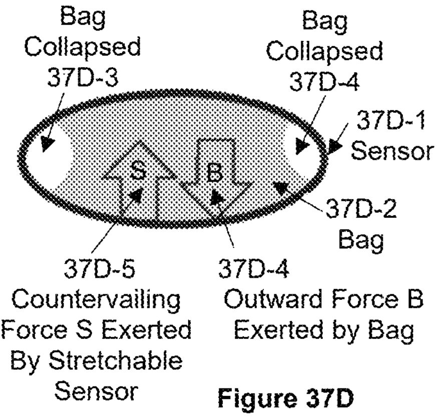
Figure 37D
When bag is empty and sensor not stretched, the length of the collapsed bag beneath the sensor 37E-3 is greater than the length of sensor 37E-1
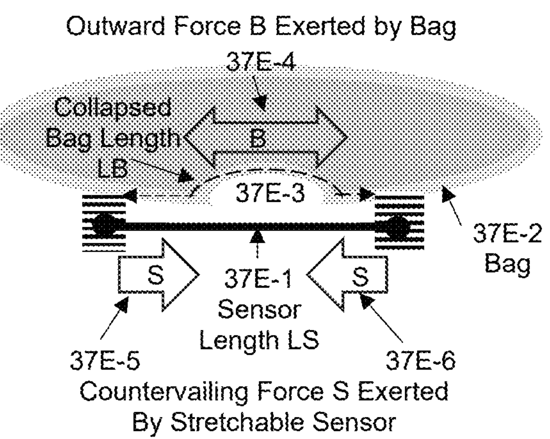
Figure 37E
Stretch Sensor Configurations And Countervailing Forces Sensor Module And Electronic Processing Module With Calibration And Fluid Level Adjustments

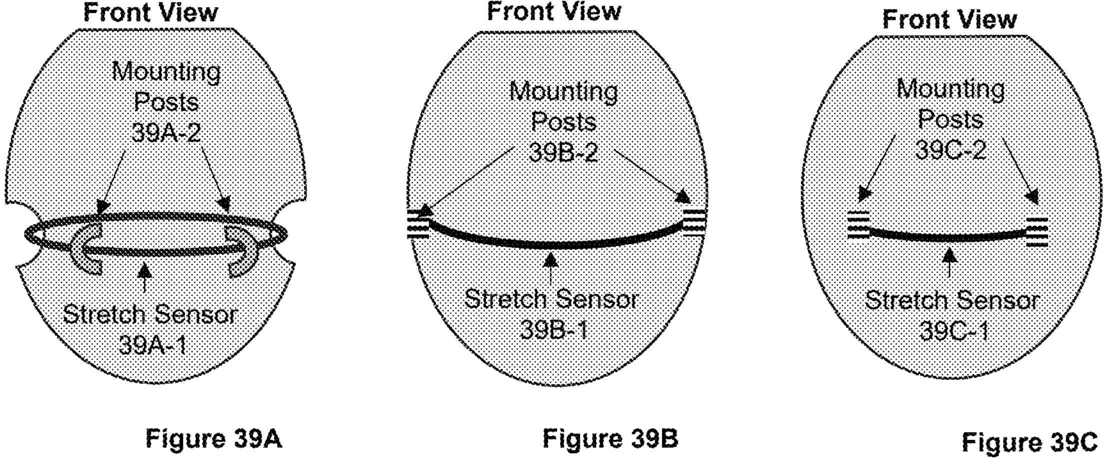
Figure 39A Figure 39B Figure 39C
Stretch Sensor Preinstalled On Ostomy Bag By Manufacturer Using Mounting Posts
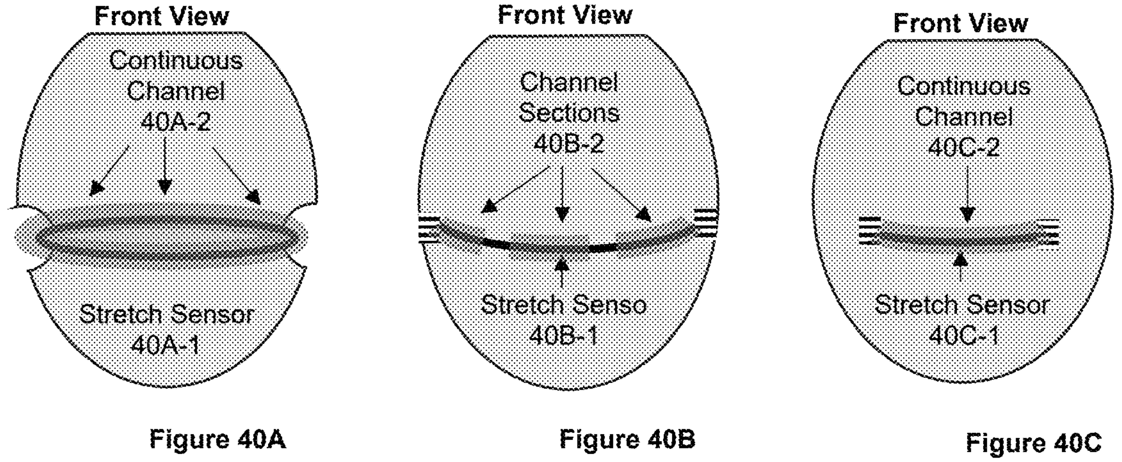
Figure 40A Figure 40B Figure 40C
Stretch Sensor Preinstalled By Manufacturer Into Channels Integrated Into The Ostomy Bag

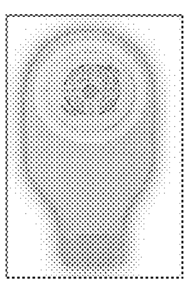
Convatec
Colostomy Bag
Figure 41A
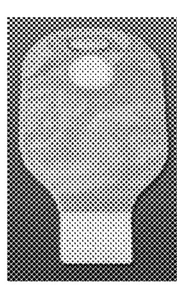
Hollister
Colostomy Bag
Figure 41B
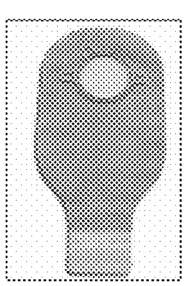
Coloplast
Colostomy Bag
Figure 41C
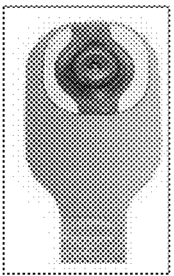
Convatec
Ileostomy Bag
Figure 41D
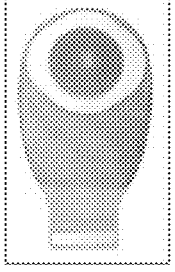
Hollister
Ileostomy Bag
Figure 41E
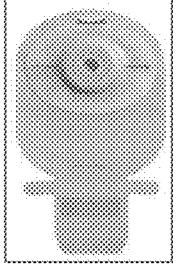
Coloplast
Ileostomy Bag
Figure 41F
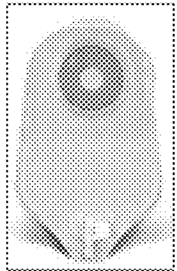
Convatec
Urostomy
Bag Figure 41G
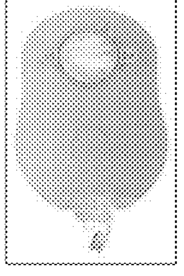
Hollister
Urostomy
Bag Figure 41H
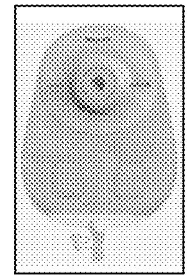
Coloplast
Urostomy
Bag Figure 41I
Types Of Ostomy Bags By Different Manufacturers External Fluid Drainage Bag by Vesco External Urinary Drainage Bag By Rush Urinary Leg Drainage Bag by Medline Wound Drainage Bag by Fistula Wound Drainage Pouch by Hollister Types Of Drainage Bags By Different Manufacturers

IV Blood Bag
Figure 43A
IV Blood Bag On Stand
Figure 43B
Figure 44A Figure 44B Figure 44C
IV Medication Bag
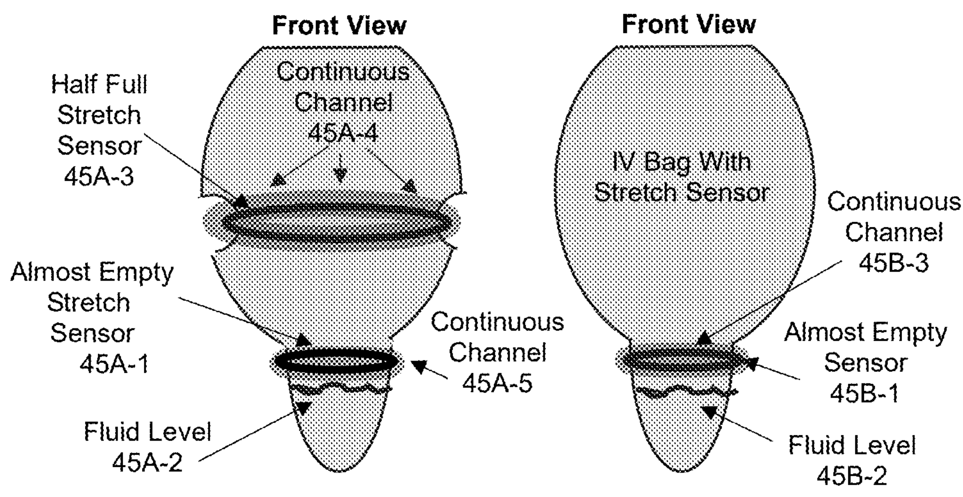
IV Bag With Two Stretch Sensors
Figure 45A
IV Bag With One Stretch Sensor
Figure 45B

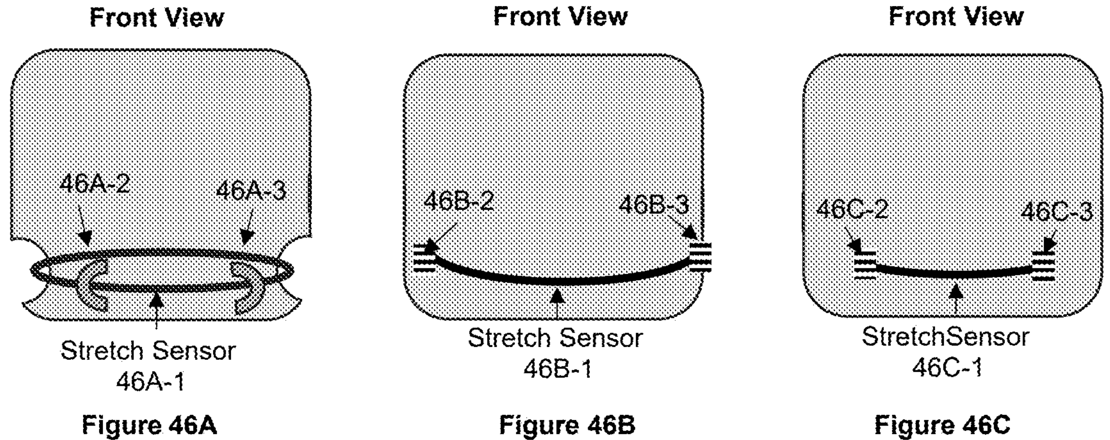
Figure 46A Figure 46B Figure 46C
Stretch Sensor Preinstalled On Medication Or Blood Bag By Manufacture Using Mounting Posts
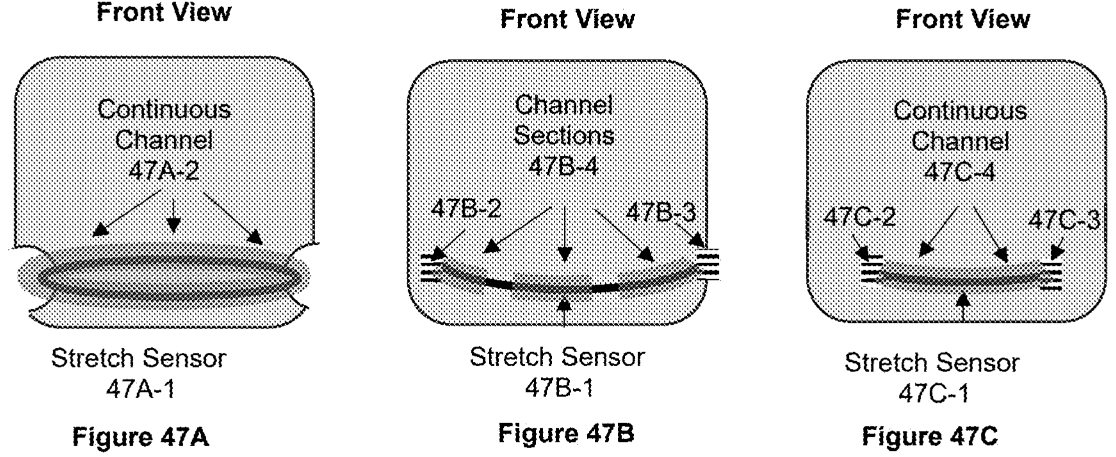
Figure 47A Figure 47B Figure 47C
Stretch Sensor Preinstalled By Manufacturer Into Channels Integrated Into A Medication Or Blood Bag

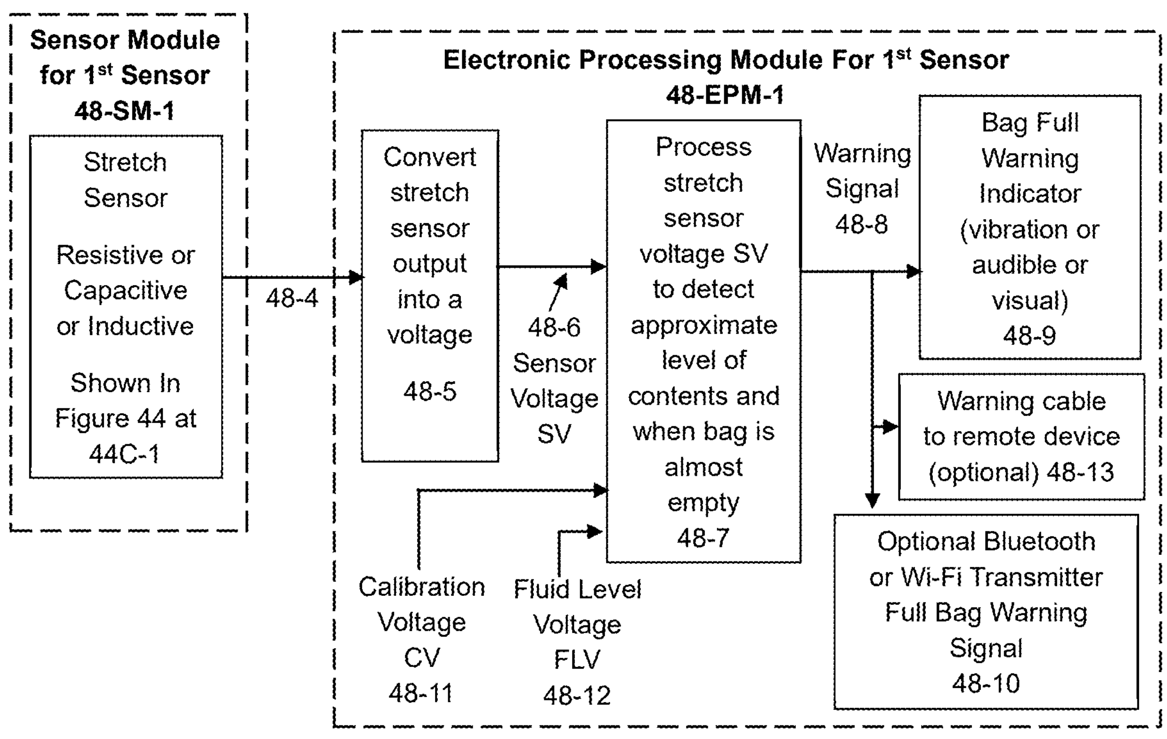
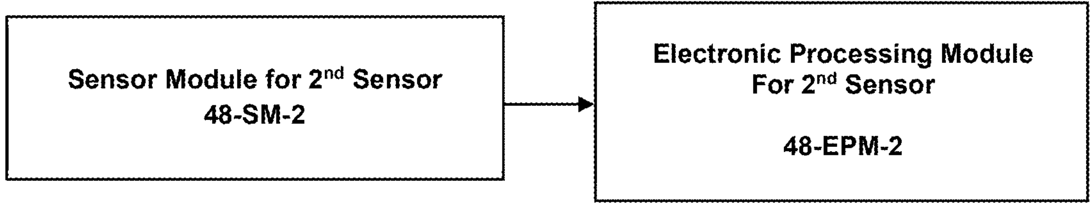
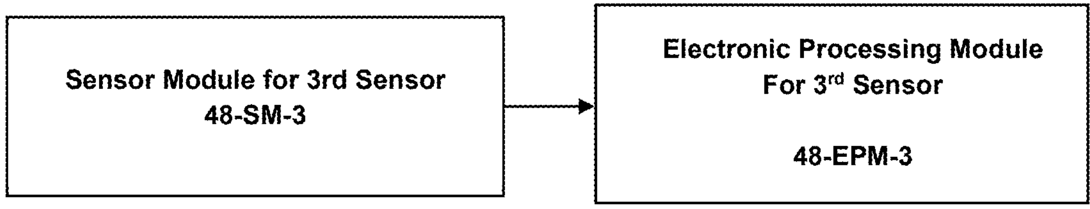
Warning System For Bags Dispensing Medication Or Blood
Figure 48

SENSOR FOR DETECTING THE FILL STATE OF A MEDICAL FLUID BAG

CROSS REFERENCE TO RELATED APPLICATIONS

This application claims priority to a co-pending U.S. Provisional Patent Application Ser. No. 63/866,038 filed Aug. 18, 2025, entitled "Urostomy Bag Full Sensor".

TECHNICAL FIELD

This patent relates to checking the contents of ostomy, drainage, or wound bags to determine if they are almost full and need to be emptied, or if IV bags dispensing medication or blood are almost empty and need to be replaced.

BACKGROUND

When individuals need to urinate or move their bowels, pressure in the bladder or the gastrocolic reflex in the colon provides signals to the brain that their body needs to eliminate waste product. However, patients wearing ostomy (urostomy, colostomy, or ileostomy) bags after surgery do not have any warning as to when this waste product empties into the bag or when the bag needs to be emptied. This can lead to separation of the bag from the patient and embarrassing spills. FIG. 1 is a picture of an ostomy bag at 1-1. The bag connects to the body at a stoma located at 1-2. Waste entering the bag collects at 1-3. A drain valve located at the bottom of the bag at 1-4 is used to remove the waste when the bag needs to be emptied.

Ostomy products are designed for three types of stomas: colostomies, ileostomies, and urostomies. Colostomies are formed from the large intestine, and the output is often thicker or even formed stool. Ileostomies are formed from the lowest part of the small intestine, and the output is liquid stool which can sometimes be more frequent than a colostomy. The final type of ostomy is a urostomy, which is done when the bladder must be removed or bypassed due to injury or disease. Urostomy output consists of urine and mucus.

FIG. 2 is a photograph of a urostomy bag, at 2-1, manufactured by Convatec. Such bags are manufactured out of a plastic type waterproof material that is flaccid, foldable and collapsible much like a Ziplock food storage bag. FIGS. 1 through 7 are images of urostomy bags. These bags are not stretchable and are designed to hold a specified volume of liquid.

For illustration purposes, the bags in FIGS. 1 through 7 have been attached to a wooden board using the identical mounting wafer used to attach the bag to a human. The wafer attachment point is shown in FIG. 3 at 3-2 and in FIG. 4 at 4-2. A front view of the wafer mount, without the bag attached is shown in FIG. 3 at 3-3. A hole at the top of the wooden board enables the bag's fill port, in FIG. 2 at 2-2, to be filled with liquid (water), as illustrated at 2-3, in the same manner as urine would normally flow into the bag through the stoma.

FIGS. 2 and 3 show how a bag would rest on a body when a person is in a standing position or bending back. FIG. 4 shows how a bag would move forward, at 4-3, and away from the body as a person bends forward. FIGS. 5, 6 and 7 show how a bag can bend, twist, fold, and crinkle as a person bends or leans to the left, right, or sits in a chair.

Unfortunately there are no devices in the prior art that can warn a person that their bag is full and needs to be emptied that work for all the bag positions shown in FIGS. 2 through 7. Working is defined as not only detecting when a bag is almost full, but also not falsely indicating that a bag is full when it is not. Such false calls, or the failure to detect when a bag is full, can result from a bag twisting, folding, and crinkling as a person changes position.

There are literally an infinite number of possible complex bag shapes which must be tolerated by a warning device. Since it is difficult to capture these contorted shapes in simple line drawings, photographs of actual urostomy bags in such positions are provided to describe the complexity of the problem, where the prior art fails, and how the device in this invention works.

The photograph in FIG. 2 shows the front view of a liquid (water) filled urostomy bag oriented to simulate a person in a vertical standing position. The bag has a bend at 2-4, a front bulge at 2-5, and a side bulge at 2-6. The side view photograph in FIG. 3, with the bag in the same vertical position, shows a first bend at 3-4, a second bend at 3-5, and a front bulge at 3-6. When a person bends forward, the bag only attached at 4-2, swings forward. This redistributes the liquid within the bag, changing the bag's shape, to a bend at 4-4, a straight section at 4-5, and a bulge at 4-6. The two side view images of FIGS. 3 and 4 have very different shapes.

When a person leans to one side, tilting the bag to the left, as shown in FIG. 5, the liquid contents. (water) redistributes within the bag. This creates an indentation on the right side of the bag at 5-3, a straight section on the right at 5-4, and a side bulge on the left at 5-5. If the person now leans to the other side, tilting the bag to the right, as shown in FIG. 6, the liquid contents, (water) moves to the other side of the bag, causing an indentation on the left side of the bag at 6-3, a straight section on the left at 6-4, and a bulge on the right at 6-5. It is obvious from the photographs that the shape of the bag changes drastically between FIG. 5 and FIG. 6.

The photograph in FIG. 7 simulates a person in a sitting position, in which the bag would bend below the waist. Bending the bag, as shown in the picture caused a first irregular shape at 7-3, twists and bends at 7-4, and a second irregular shape at 7-5.

Having shown examples of these actual complex bag shapes we will now discuss prior art warning devices and limitations thereof.

As a first example, inventor Davis in UK patent application GB 2636256 discloses in the abstract "An alert device for an ostomy bag comprising a housing configured to hang over the bag, a tension cord attachable to the housing and positioned across the front of the bag, a sensor mechanism connected to the tension cord and a notification module housed within the device and configured to alert the patient via vibration/audible alarm when the bag is full."

In the detailed description of the patent, in paragraph 0029 Davis writes "The method or process of using the present discloser is such that, the user will take the Ostomy bag and the present disclosed device, and unhook the tension cord from the tension housing, then place the device over the Ostomy bag and then bring the tension cord across the front of the Ostomy bag and secure by hooking in place on the main body." For reference, FIGS. 8 and 9 are illustrations of the device taken from prior art FIGS. 1 and 2 in Davis's patent application.

While Davis's device may work if a person is standing, such that the bag is in a vertical position as shown in FIGS. 2 and 3, the unit can fail if the person changes position such as bending forward, right, left or is in a sitting position. For example, if the person bends forward, causing the bag to move away from the person as shown in FIG. 10 at 10-1, the bag could push against the tension cord in FIG. 11 at 11-6, falsely triggering the device and alerting the patient that the bag is full, even if the level of urine is below the intended trigger level. Furthermore, the rigid frame would be problematic in a sitting position, interfering with a person's legs, as Illustrated in FIG. 11. FIG. 11 at 11-1 is a front view illustration of an ostomy bag on a person. A side view illustration shows the Davis rigid frame at 11-2, the bag at 11-3, the person's torso at 11-4, the person's legs at 11-5, and the tension cord of the Davis device at 11-6. When the person sits down, the frame, shown at 11-2, would interfere with the person's legs at 11-5.

As a second example, inventor Kriscovich in Pub. No.: US 2022/0192564 A1, discloses in the abstract "a urine collection bag, system, and methods directed to automated measurement of a quantity of urine. The urine collection system can include the urine collection bag, a catheter, and flexible drainage tubing. The urine collection bag can include a collection area, force sensors, and circuitry configured to determine the volume of urine in the collection area based on pressure or weight measured by the force sensors, and the specific gravity of the urine."

In claim 1 Kriscovich writes "one or more force sensors coupled to or integrated into the urine collection bag, the one or more force sensors configured to measure a pressure or a weight of the urine collected within the collection area;" For reference, FIGS. 12A, 12B, and 12C contain prior art FIGS. 1, 2A, and 2B from the Kriscovich publication. Simply coupling a sensor to the exterior surface of a bag, as shown in FIGS. 12B and 12C at 210 will not work without the senor being attached to an external reference surface to produce a countervailing force.

In paragraph 0058 Kriscovich writes "In some embodiments, a countervailing force may be present on force sensor 210. Such a countervailing force may be necessary to stabilize force sensor 210, so that it does not accelerate or move, and can therefore measure the strain or pressure accurately." The use of the language "in some embodiments, a countervailing force may be present" suggests that there are other embodiments in which a countervailing force is not required. This is misleading because the Kriscovich invention will not work without a countervailing force applied to sensor 210, and no countervailing forces are shown in FIG. 12A, 12B, or 12C.

To best explain what a countervailing force is, how it works, and why it's required, consider a person standing on a floor scale (force sensor), as illustrated in FIG. 13A at 13A-1. The person exerts a downward gravitational force onto the top of the scale at 13A-2. The floor beneath the scale exerts an equal counteracting upward force to the bottom of the scale at 13A-3. If this counteracting force was not applied the scale would fall through the floor. This counteracting force is frequently referred to as a countervailing force. What happens inside the scale is that a spring or some device compresses in response to the forces applied to the two exterior (top and bottom) surfaces of the scale. In FIG. 13B, a force sensor at 13B-1 is attached to a wall at 13B-2. A horizontal force is applied to the force sensor at 13B-3. In response, the wall exerts an equal but opposite countervailing force to the back of the sensor at 13B-4. In response to forces applied from both sides, the sensor compresses, enabling it to measure the applied force.

To understand the importance of a countervailing force, consider the sensor in FIG. 13 at 13C-1 glued to one side of a curtain at 13C-2, hanging from a rod at 13C-3. If a horizontal force is applied to the front surface of the sensor at 13C-4, the sensor will just move and sway with the curtain because there is no countervailing force to stop it. Without a countervailing force, the sensor will not be able to measure the force applied to it.

Now consider the urostomy bag shown in FIG. 13D at 13D-1, with force sensor 13D-2 attached to the outside of the bag at 13D-3. As the bag fills with urine to a level 13D-4, gravitational forces cause the urine to exert an outward force onto the interior surface of the urostomy bag at 13D-5. The bag responds with a countervailing equalizing force at 13D-6, such that the bag and urine always remain in a state of equilibrium. Without a reference surface attached to the force sensor at 13D-2, the sensor will be free to move as the bag fills with urine and the sensor will not be able to measure any forces applied to it.

The sensor shown in FIG. 13D at 13-2 is attached to the exterior surface of the bag the same way Kriscovich sensor 210 is attached to the bag in FIG. 12C (same as FIG. 2B in the Kriscovich publication), yet Kriscovich writes in paragraph 0057 "FIG. 2B displays the functioning of a force sensor 210 located on a side wall 215 of urine collection bag 120, according to some embodiments. In this example, urine collection bag 120 is filled with urine 250, which exerts a pressure on side wall 215 of bag 120. Side wall 215 may expand and/or strain against force sensor 210." Kriscovich's description given in paragraph 0057 cannot work as explained without a reference surface attached to sensor 210 to provide a countervailing force. As illustrated by Kriscovich in FIG. 12C, sensor 210 will simply move with side wall 215, unable to measure any force applied to it.

Unfortunately, attaching a reference surface to a sensor attached to an ostomy bag, such as the urostomy bag shown in FIGS. 2 through 7, is not an option because this would require some sort of frame to prevent the sensor from moving. Such a frame may be uncomfortable to wear, limit a person's range of motion and interfere with the various bag positions shown in FIGS. 2 through 7.

As a third example, inventor Stalmann, in Australian Application AU 2021105360 A4, discloses in the abstract: "The present invention relates to an alarm generating system for use with a collection bag worn by a user for collecting a bodily material from the user, such as an ostomy bag, a catheter bag, or a drainage bag. The system comprises at least one sensor attached to the collection bag to detect the shape of the bag; a control system to receive signals from at least one sensor; and at least one alarm generating device. Upon receipt of one or more signals from the at least one sensor indicate that the bag is nearly full, the control system activates the at least one alarm generating device to cause the at least one alarm generating device to generate a vibratory alarm."

On page 3 paragraph 15, Stalmann writes "In some forms, the sensor comprises a hinge sensor. In other forms, the sensor comprises a capacitive sensor. In yet other forms, the sensor comprises an inductive sensor."

On page 6 paragraph 30, Stalmann writes, referring to FIG. 14A, "The hinge sensor 10 is located on the bag 200 so that the corner of the hinge sits adjacent to a side edge of the bag 200." Later in the same paragraph, he writes "As the bag fills, the shape of the bag changes, causing the first and second side surfaces of the bag to move away from each other."

On page 7 paragraph 10, Stalmann writes "Once the hinged first and second parts of the hinge sensor 10 are opened to a predetermined extent, such as when a predetermined angle is formed between the first and second parts, an electrical circuit is closed within the hinge sensor 10, which causes the sensor 10 to generate at least one signal that is sent to the control system 20. In preferred forms, the maximum angle formed between the first and second parts of the sensor 10 is an acute angle and is typically between 45 and 70 degrees, preferably between 50 and 60 5 degrees, such as 55 degrees."

Stalmann, writes in claim 1

"An alarm generating system for use with a collection bag to be worn by a user for collecting a bodily material from the user, the system comprising:

at least one sensor attached to the collection bag to detect the shape of the bag;

a control system to receive signals from the at least one sensor; and at least one alarm generating device comprising at least one movable component that is locatable on a person's skin during use;

wherein upon receipt of one or more signals from the at least one sensor that indicate that the bag is nearly full, the control system causes the at least one alarm generating device to generate a vibratory alarm by vibrating the at least one movable component."

Detecting a change in shape as a means of measuring urine volume is problematic because the bag may also change shape when a person changes position, as illustrated in FIGS. 1 through 7. The shape of the bag may also be affected if placed into a body-wrap with a pocket for the ostomy bag, such as the one shown in FIG. 15 manufactured by Convatec's Ostomy Secrets division. The body-wrap may cause the bag to crease if the person bends forward or sits down, and the stitched edges of the pocket may restrict or interfere with the hinge mechanism shown in FIG. 14A.

SUMMARY

The invention addresses the need for and describes a novel method to implement a low cost ostomy full bag warning device. Other applications of the invention include producing a warning signal when other types of medical bags, such as wound drainage bags that collect fluids from surgical sites, become full and need to be emptied or when the fluid levels in bags containing medication or blood connected to a patient through an IV line are almost empty and need to be replaced. Unique to the sensor incorporated in the warning device is that it adapts to the shape of a fluid filled bag. The sensor can be easily attached to the outside of bags currently in commercial production or integrated by a manufacturer onto a bag and the sensor does not need to be attached to an external reference surface to generate a countervailing force. An electronic module attached to the sensor can be programmed to produce a warning signal when an ostomy, or drainage bag is full or when a bag dispensing medication is almost empty.

BRIEF DESCRIPTION OF THE DRAWINGS

The description below refers to the accompanying drawings, of which:

FIG. 13A, 13B, 13C, 13D are illustrations showing how countervailing forces work;

FIG. 16A is a photograph of an empty urostomy bag showing a resistive stretch cord sensor wrapped around a bag;

FIG. 16B is an illustration showing the sides of a flaccid bag collapsed to fit within the perimeter of a cord sensor;

FIG. 17 is an illustration showing the resistance of a stretch cord sensor measured by an ohmmeter;

FIG. 30A is a photograph showing a full urostomy bag in a vertical position;

FIG. 30B is an illustration showing the resistance of the stretch cord sensor corresponding to the fill level and vertical bag position shown in FIG. 30A FIG. 31A is a photograph showing a full urostomy bag tilted approximately 45 degrees;

FIG. 31B is an illustration showing the resistance of the stretch cord sensor corresponding to the fill level and tilt angle shown in FIG. 31A;

FIG. 32A is a photograph showing a full urostomy bag tilted approximately 45 degrees;

FIG. 32B is an illustration showing the resistance of the stretch cord sensor corresponding to the fill level and tilt angle shown in FIG. 32A;

FIGS. 37A, 37B, 37C, 37D and 37E show stretch sensor configurations and countervailing forces;

FIGS. 39A, 39B and 39C show sensors preinstalled on an ostomy bag by the manufacturer using mounting posts;

FIGS. 40A, 40B and 40C show sensors preinstalled by the manufacturer into channels integrated onto the ostomy bag;

FIGS. 41A through 41I are photographs showing types of ostomy bags by different manufacturers;

FIG. 43A is a photograph showing an IV blood bag;

FIG. 43B is a photograph showing an IV blood bag on a stand;

FIGS. 44A,44B, and 44C are photographs showing IV medication bags;

FIG. 45A is an illustration showing an IV bag with two sensors;

FIG. 45B is an illustration showing an IV bag with one sensor;

FIGS. 46A, 46B, and 46C are illustrations showing sensors preinstalled on medication or blood bags by the manufacturer using mounting posts;

FIGS. 47A, 47B, and 47C are illustrations showing sensors preinstalled by manufacturer into channels integrated onto a medication or blood bag;

FIG. 48 is a block diagram for a warning system for bags dispensing medication or blood.

DETAILED DESCRIPTION OF ILLUSTRATIVE EMBODIMENTS

The warning device(s) described and shown herein serve to monitor and check if an ostomy, drainage, or wound bag is almost full and needs to be emptied or if an intravenous (IV) bag dispensing medication or blood is almost empty and needs to be replaced.

The warning device is designed to attach to any commercially available ostomy, drainage, or medication dispensing bag made of lightweight soft waterproof plastic, which is flaccid, foldable and collapsible much like a Ziplock food storage bag.

FIGS. 1 through 7 are images of prior art urostomy bags. These bags are not stretchable and are designed to hold a specified volume of liquid.

The new and improved warning device described herein incorporates a unique sensor composed of a low force stretchable material whose electrical resistance, or capacitance, or inductance changes as the material is stretched. The material can be made of rubber, fabric, or any flexible substance whose electrical resistance, or capacitance or inductance changes as it is stretched.

Figure 1:
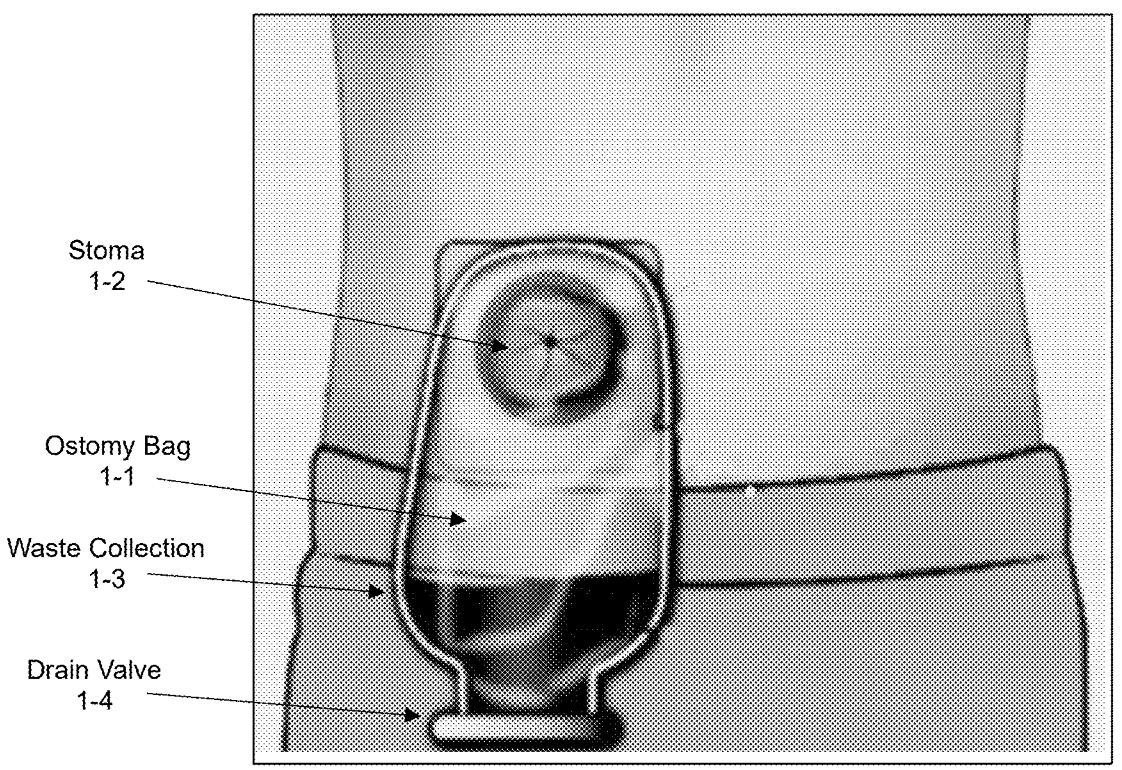
FIG. 1 is an Illustration of an ostomy bag showing where It attaches to a person.
Figure 2:
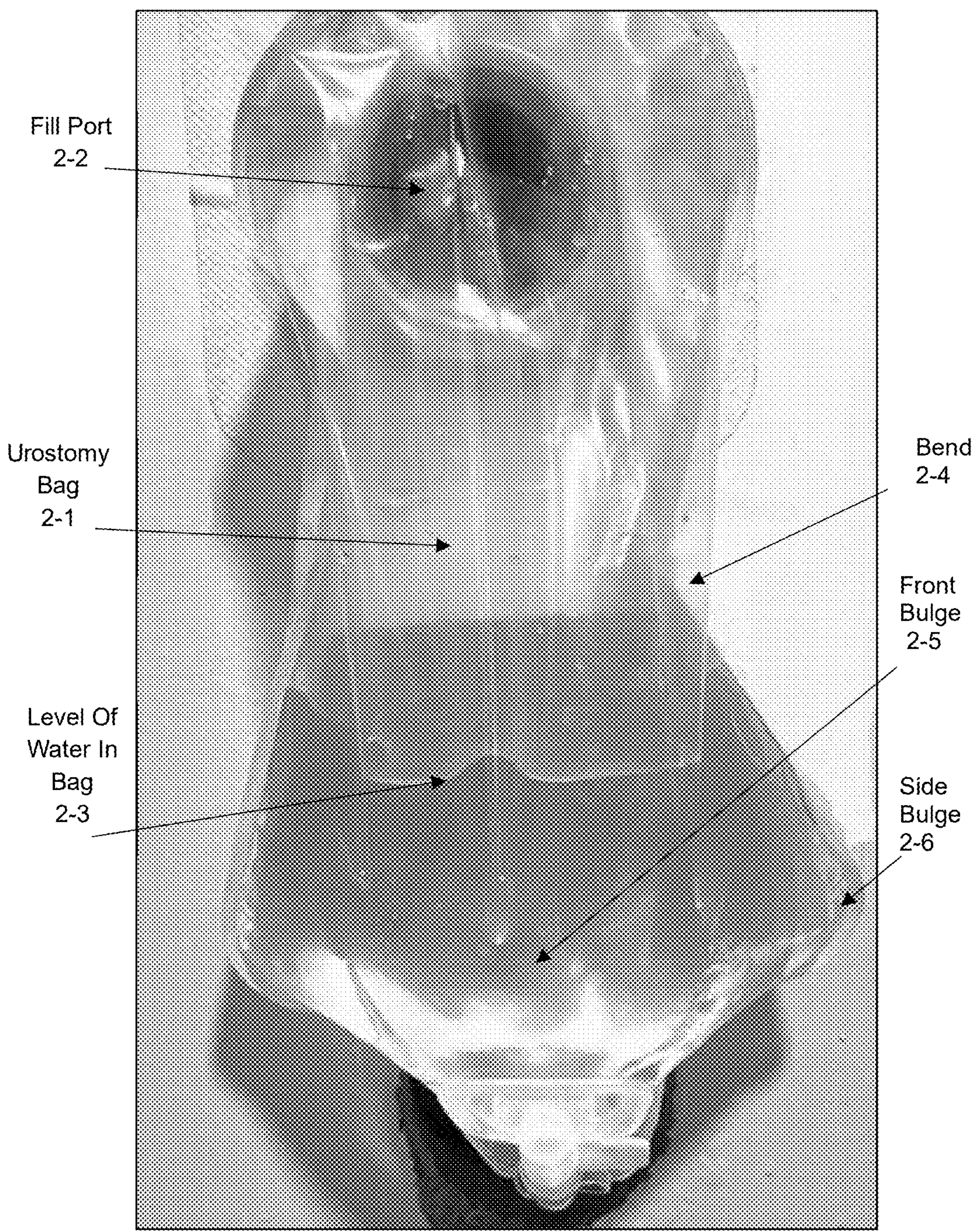
FIG. 2 is a front view photograph of a urostomy bag simulating a person in a standing position.
Figure 3:
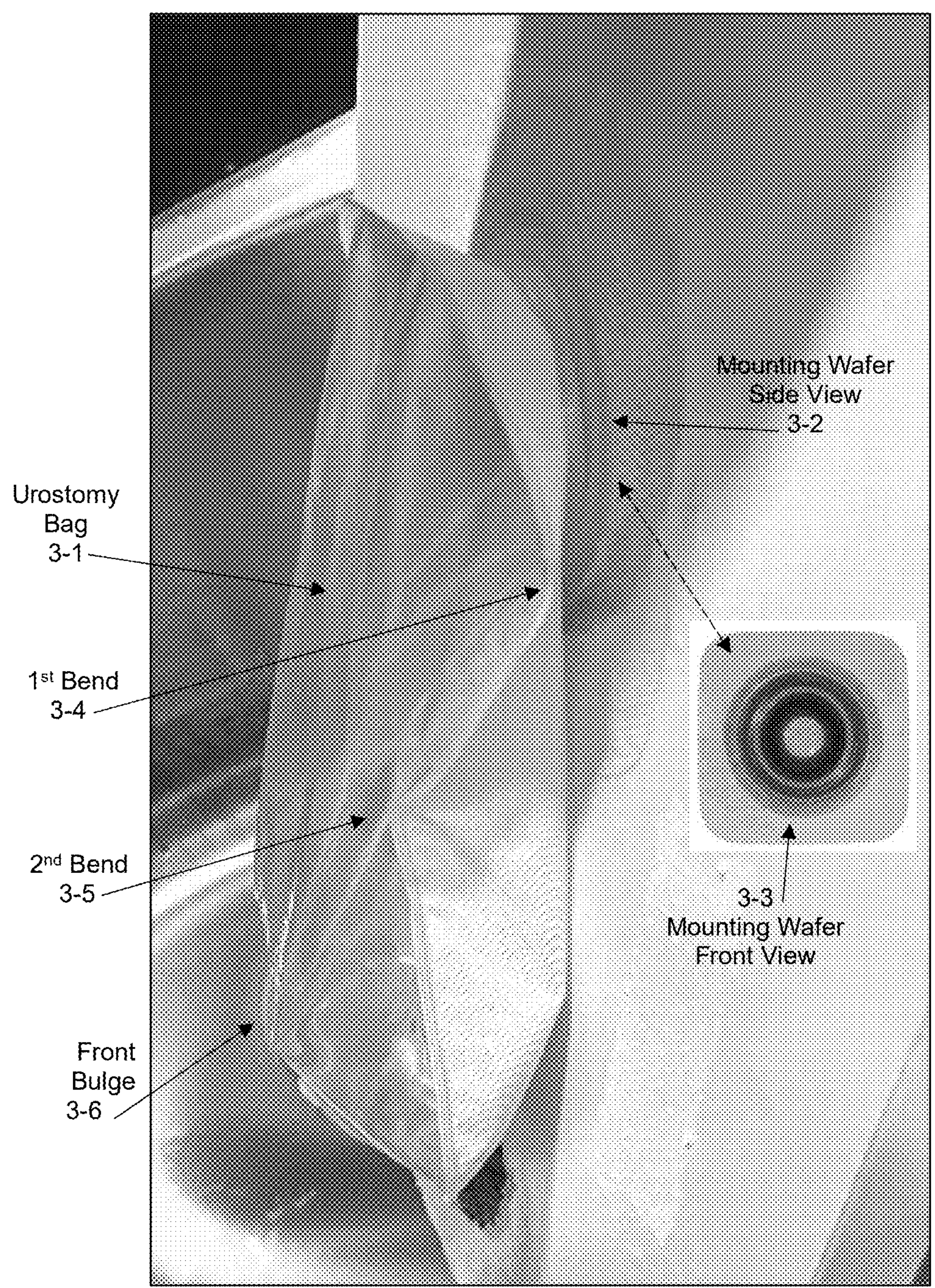
FIG. 3 is a sideview photograph of a urostomy bag simulating a person in a vertical standing position or leaning back.
Figure 4:
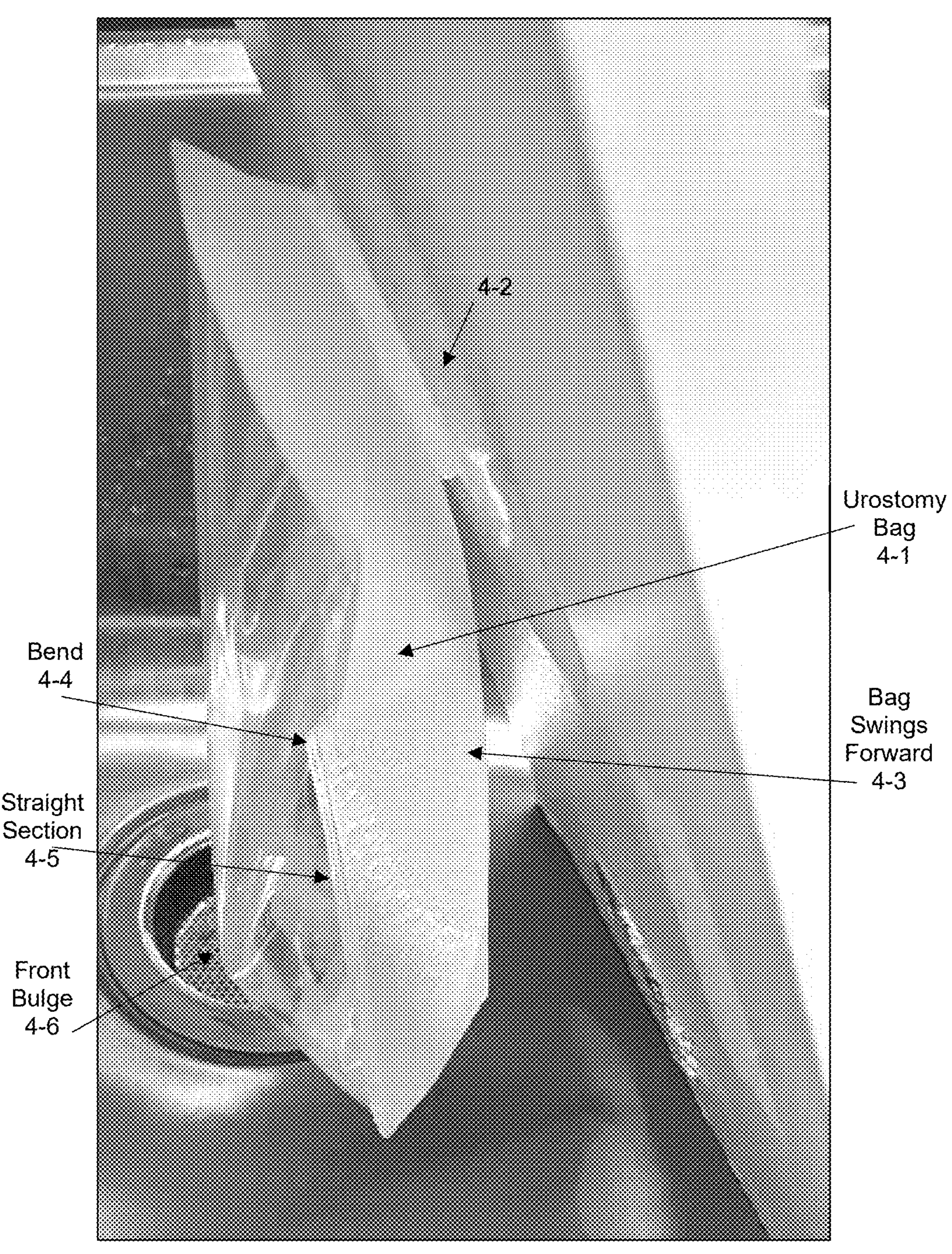
FIG. 4 is a sideview photograph of a urostomy bag simulating a person bending forward.
Figure 5:
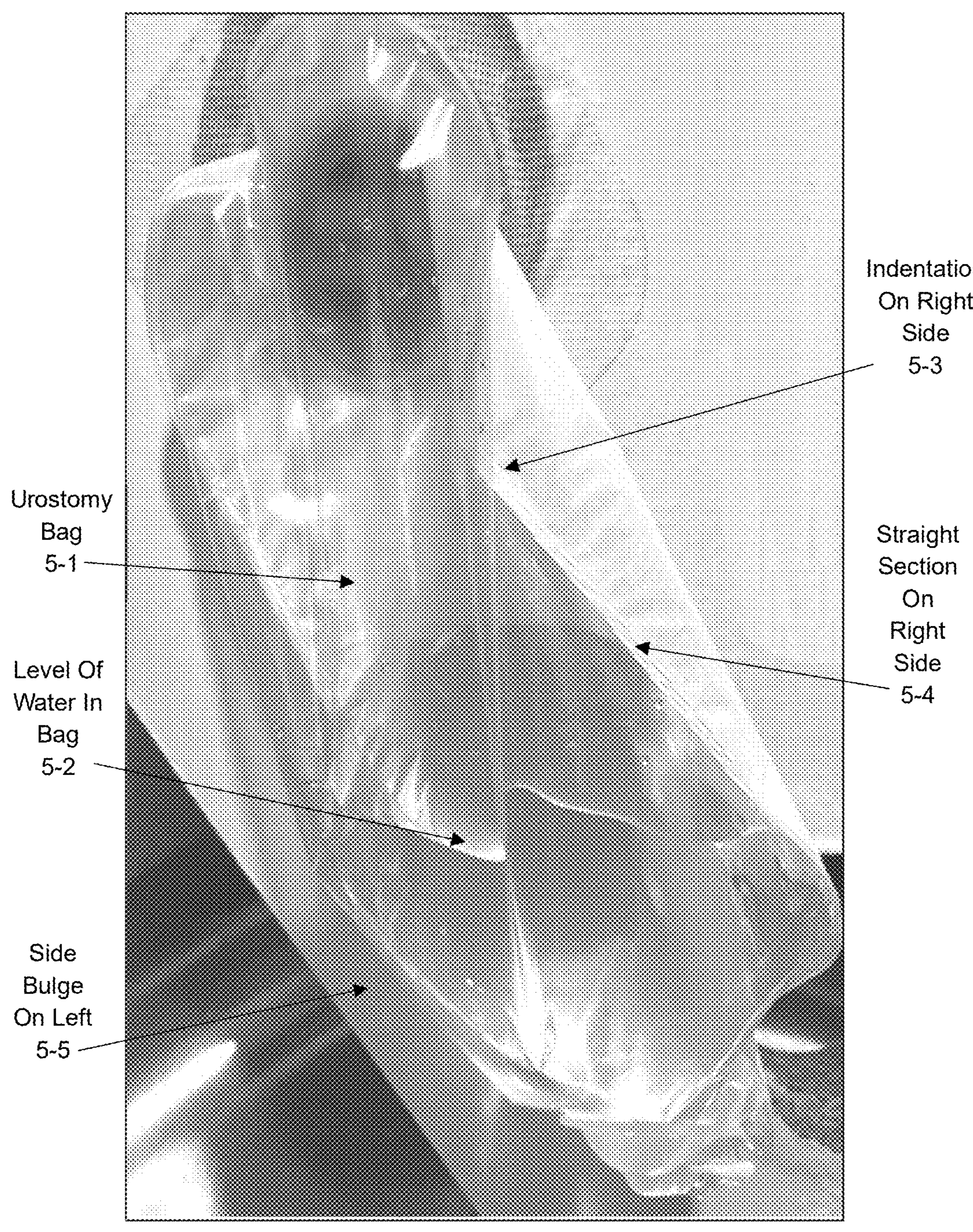
FIG. 5 is a photograph of a urostomy bag tilting left simulating a person leaning to one side.
Figure 6:
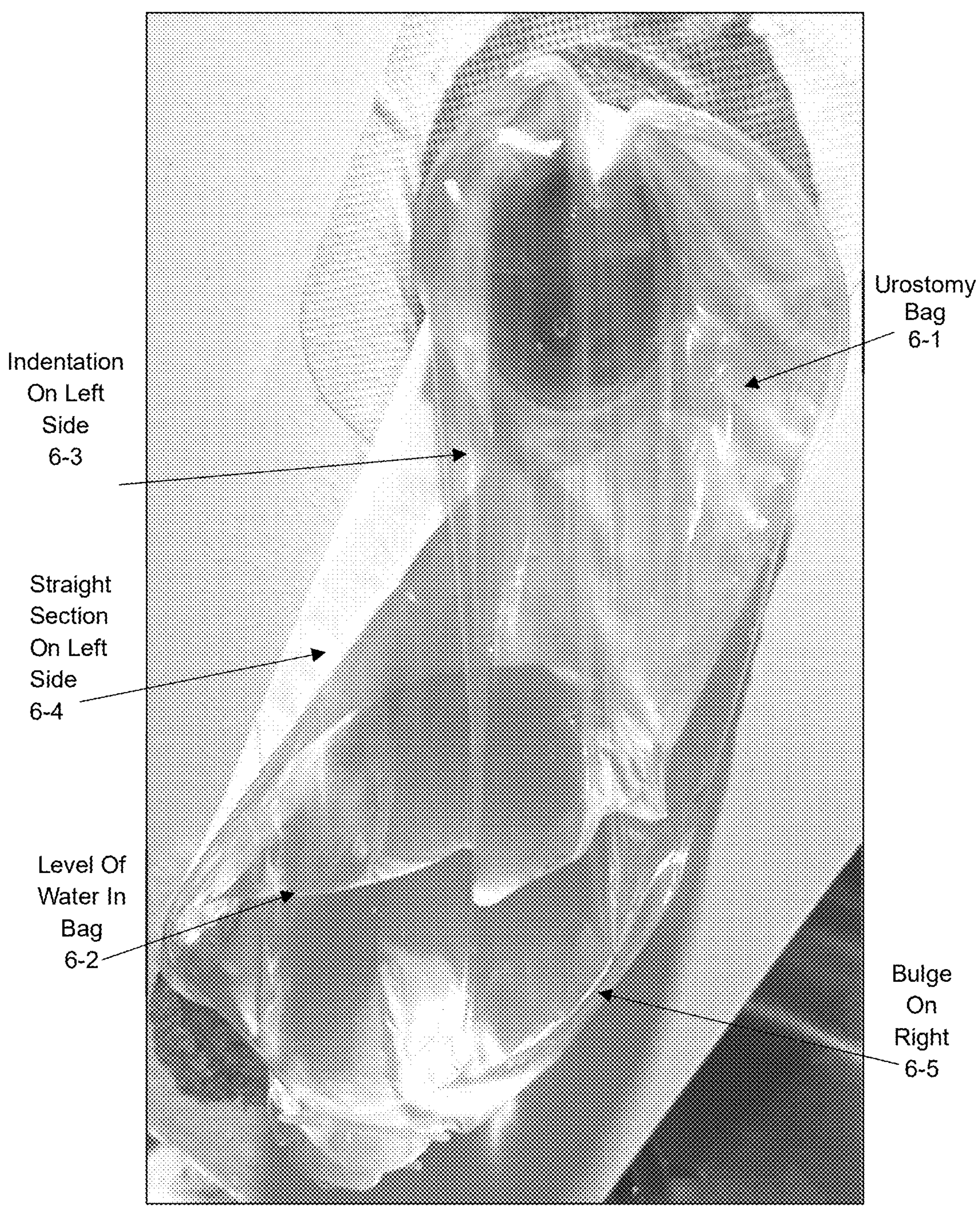
FIG. 6 is a photograph of a urostomy bag tilting right simulating a person leaning to the opposite side.
Figure 7:
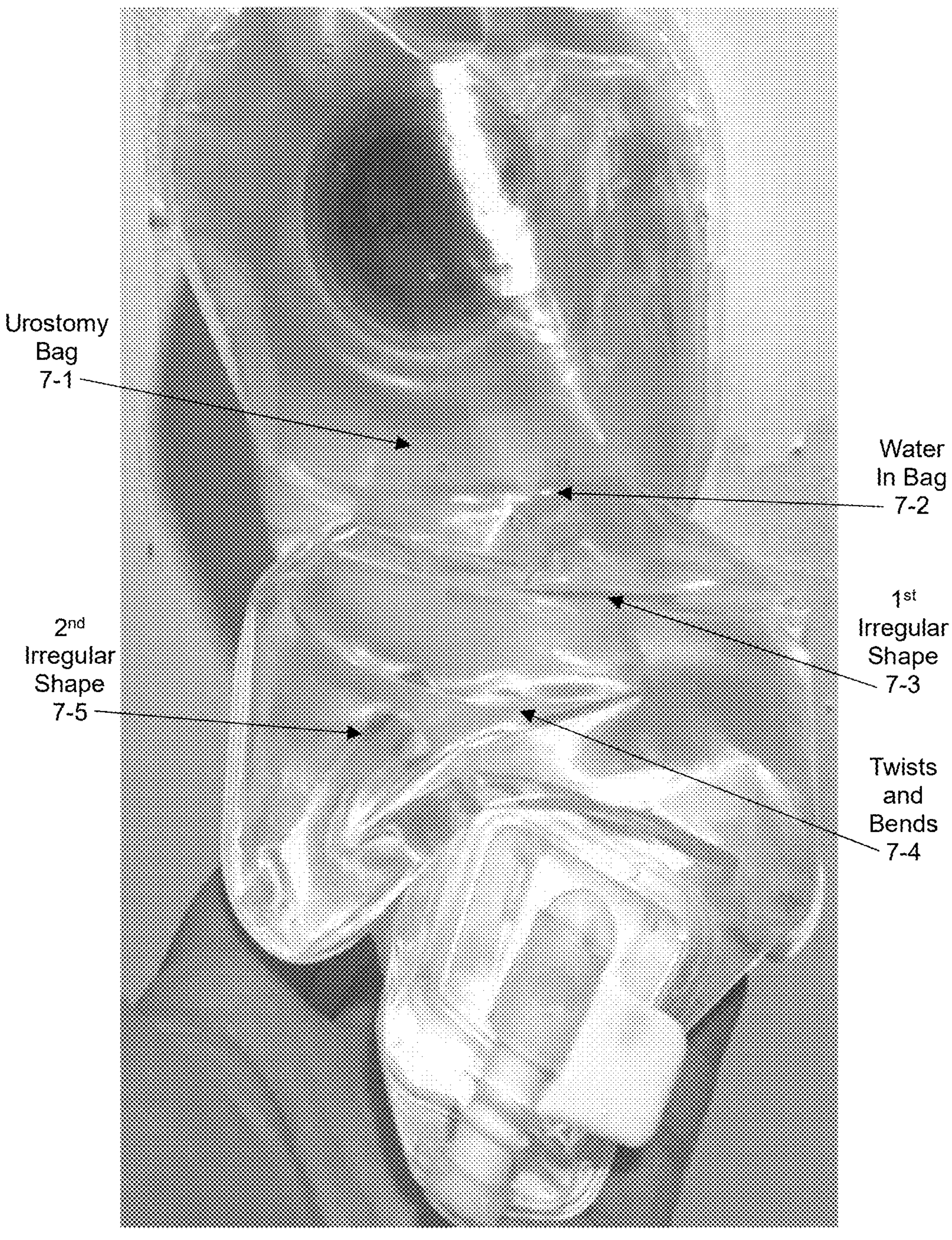
FIG. 7 is a photograph of a urostomy bag simulating a person in a sitting position.
Figure 8:
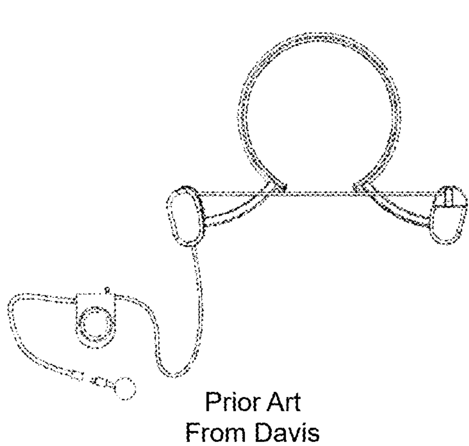
FIG. 8 is an illustration from prior art Davis UK patent application GB 2636256 showing his device.
Figure 9:
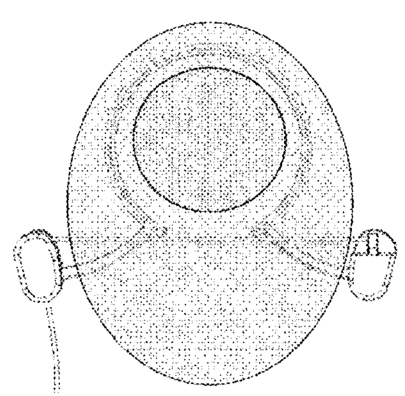
FIG. 9 is an illustration from prior art Davis UK patent application GB 2636256 showing his device.
Figure 10:
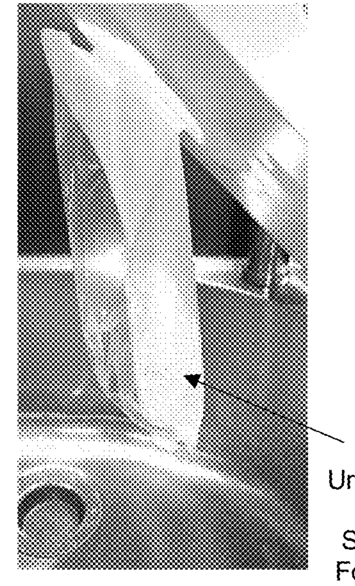
FIG. 10 is a photograph of a urostomy bag simulating a person bending forward.
Figure 11:
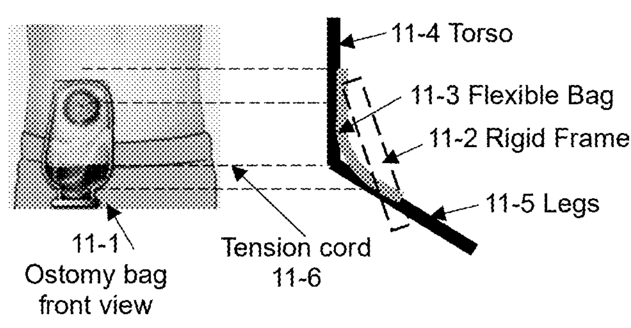
FIG. 11 is an illustration showing limitations of rigid Davis frame.
Figure 12A:
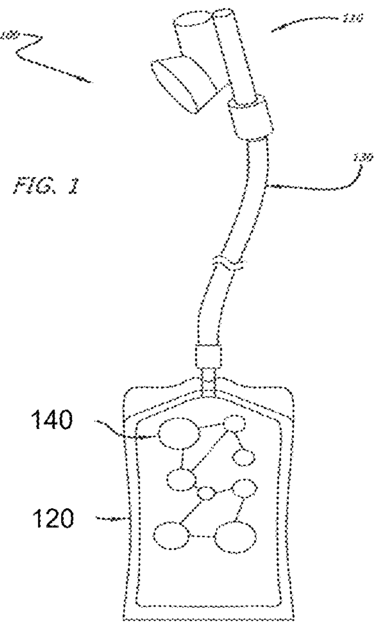
FIGS. 12A through 12C are illustrations from prior art Kriscovich publication number US 2022/0192564 A1.
Figure 12B:
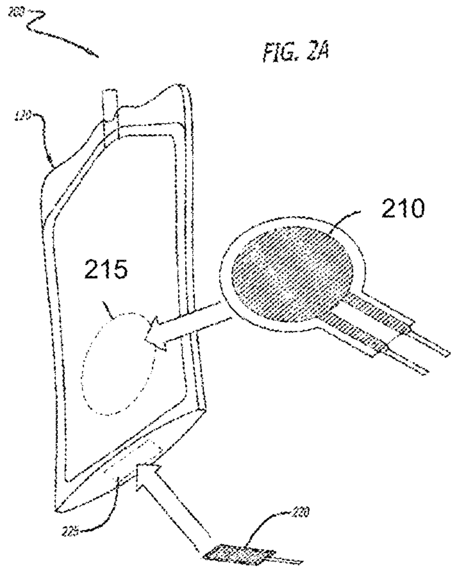
Figure 12C:
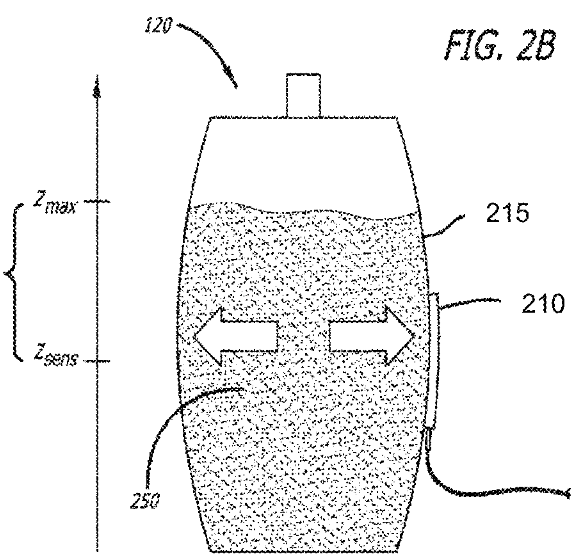
Figure 14A:
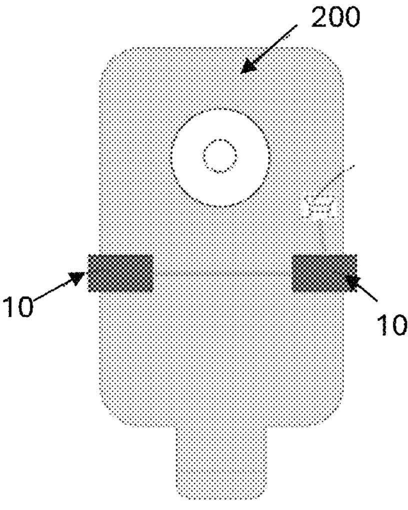
FIG. 14A through 14C are illustrations from prior art Stalmann Australian application AU 2021105360 A4 showing a hinge sensor, a capacitive sensor, and an inductive sensor, respectively.
Figure 14B:
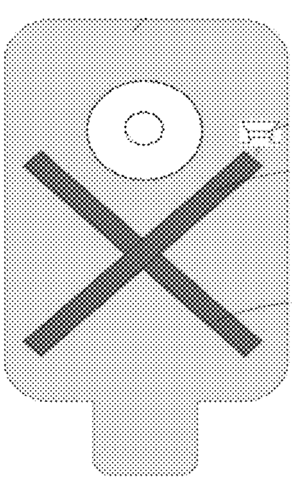
Figure 14C:
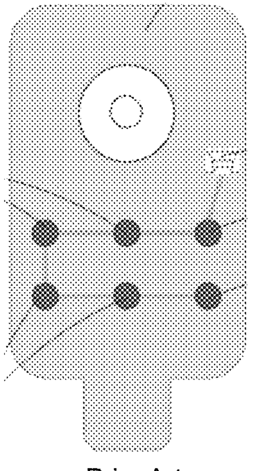
Figure 15:
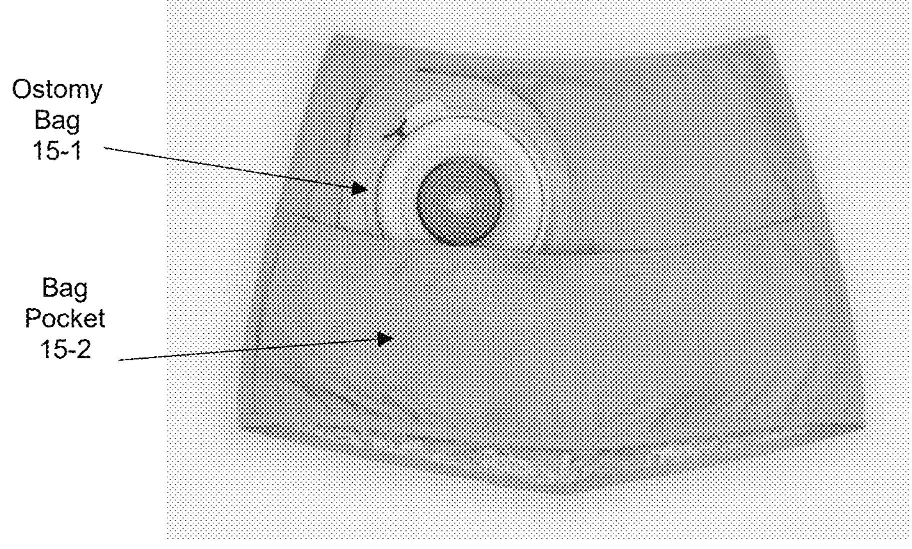
FIG. 15 is a photograph of a prior art body-wrap with pocket for ostomy bag.

A first implementation for this type of stretch sensor is illustrated in FIGS. 16A and 16B which shows a stretchable conductive cord shaped material at FIGS. 16A-1 and 16B-1 wrapped around an empty flaccid urostomy bag 16A-2, 16B-2. The sensor material is a stretchable carbon impregnated rubber cord whose electrical resistance changes as the cord is stretched. The two ends of the cord are attached by a small piece of insulating material to create a closed band that fully wraps around the entire bag. Each end of the cord is connected to a wire to enable its resistance to be measured.

In this implementation, the stretch sensor is placed at the approximate level to which the bag is to be filled. The length of the stretch sensor cord is adjusted so that it is slightly smaller than the perimeter (circumference) of the bag. Since the bag is flaccid and empty it can be easily folded or collapsed so that the bag can fit within the smaller perimeter defined by the stretch sensor, when the sensor is not stretched, as illustrated at 16A-3 and 16B-3.

It is important to emphasize that the perimeter of the bag, defined as the continuous line forming the boundary of the closed ostomy bag, is constant. It cannot increase because it is manufactured with a fixed amount of material that does not stretch. The bag can change shape, but its perimeter never changes. Therefore, as the bag fills with liquid, the bag unfolds, pressing the sides of the bag against the sensor. This stretches the sensor (but not the bag) which changes the sensor's electrical resistance.

FIG. 17 is an electrical block diagram showing an ohmmeter at 17-1 measuring the resistance of the stretch cord sensor shown in FIG. 16A at 16-1. In this example, when the bag is empty and the sensor is not stretched, the sensor measures 1762 ohms, as indicated at 17-2.

Figure 18:
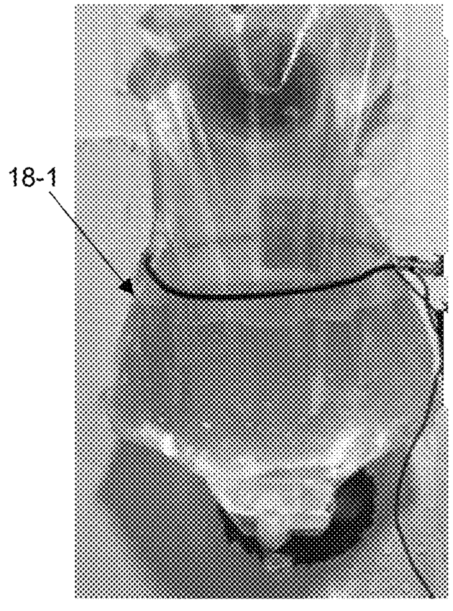
FIG. 18 is a photograph of a urostomy bag filling with liquid.
Figure 19:
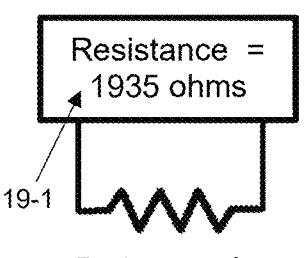
FIG. 19 is an illustration showing the resistance of a stretch cord sensor.

As the level of the liquid entering the bag approaches the level of the stretch sensor, as shown in FIG. 18 at 18-1, forces applied to the sides of the bag from the additional liquid, push the bag into the sensor. This stretches the cord and increases the cord's electrical resistance, in this example from 1762 to 1935 ohms, as shown in FIG. 19 at 19-1.

Figure 20:
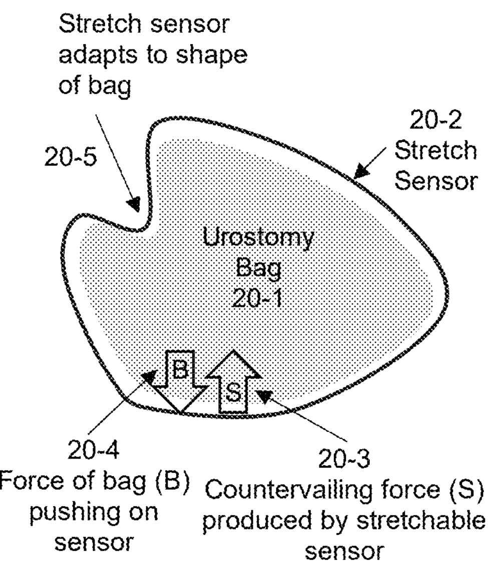
FIG. 20 is an illustration of a stretch sensor adapting to the shape of a bag and producing a countervailing force.

Unique to this sensor is that as it stretches, it produces its own countervailing force S, illustrated in FIG. 20 at 20A-3, which is equal to and opposite to the force applied to the sensor by the bag B, illustrated in FIG. 20 at 20-4. Therefore, unlike the force sensors described in Kriscovich Pub. No.: US 2022/0192564 A1, the stretch sensors described in this invention do not need to be attached to any external reference surface.

Figure 21A:
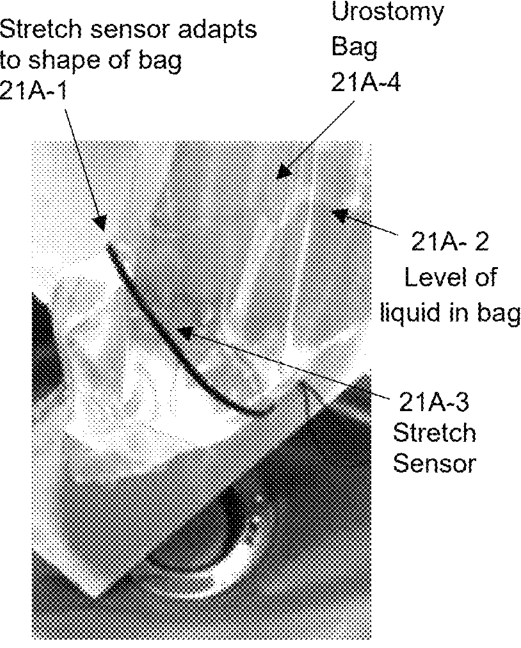
FIG. 21A is a photograph of a stretch sensor adapting to the shape of a Convatec urostomy bag.
Figure 21B:
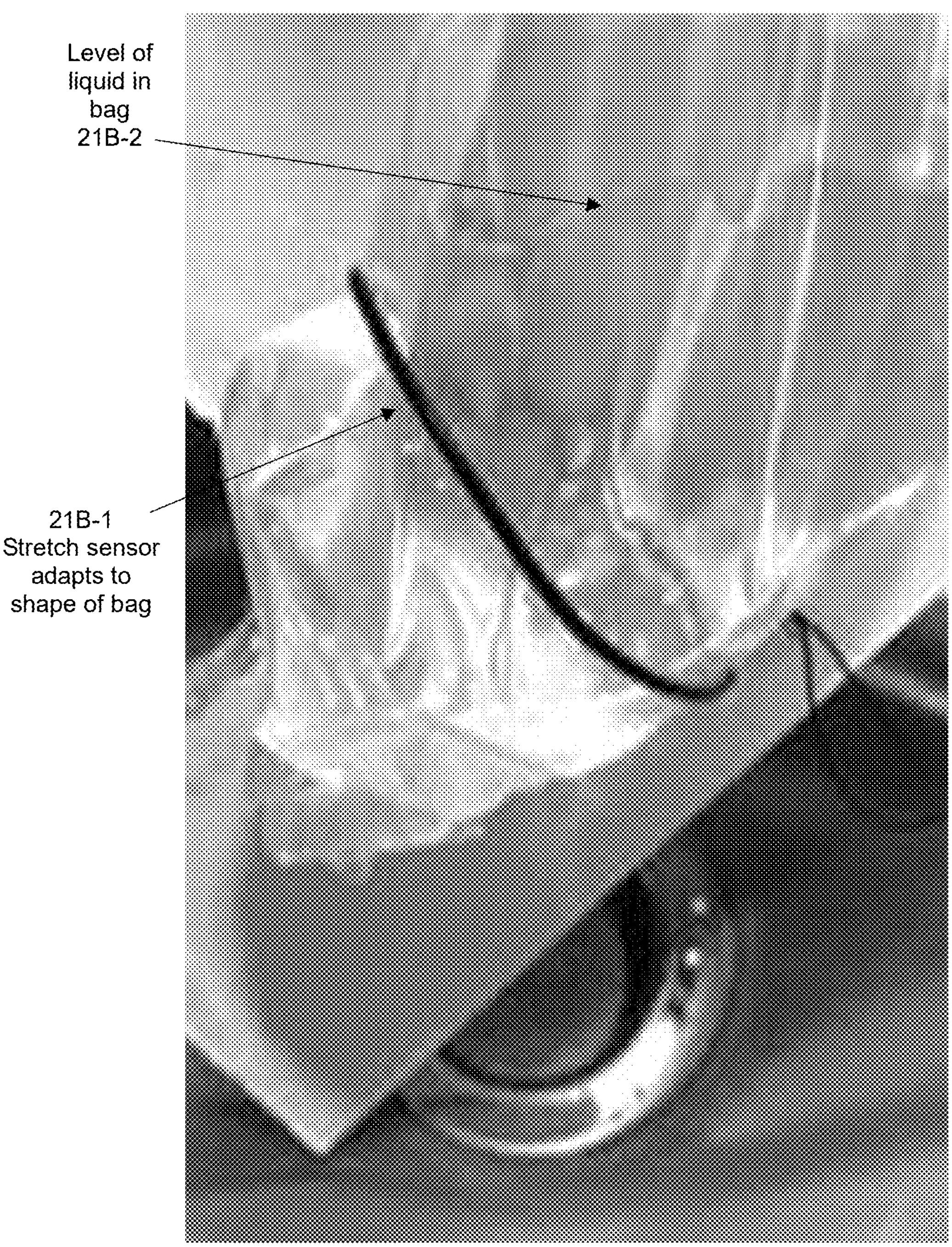
FIG. 21B is a photograph of a stretch sensor adapting to the shape of a Convatec urostomy bag tilted to the right.

Furthermore, and novel to this invention, is that the stretch sensor continually adapts to the changing shape of the bag as the volume in the bag increases. This is illustrated in FIG. 20 at 20-5, FIG. 21A at 21A-1, and FIG. 21B at 21B-1.

Figure 22:
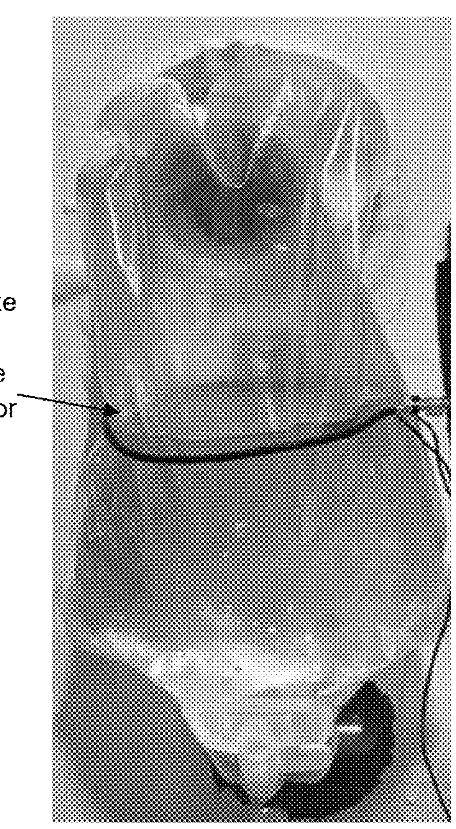
FIG. 22 is a photograph of a urostomy bag filled to approximate level of stretch cord sensor.
Figure 23:
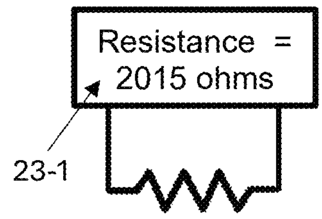
FIG. 23 is an illustration showing the resistance of a cord sensor corresponding to fill level shown in FIG. 22.

As the bag continues to fill, with the liquid now reaching the approximate level of the stretch cord sensor as shown in FIG. 22 at 22-1, this additional liquid applies more force to the sides of the bag, further stretching the cord and increasing the cord's resistance from 1935 to 2015 ohms, as shown in FIG. 23 at 23-1.

Figure 24:
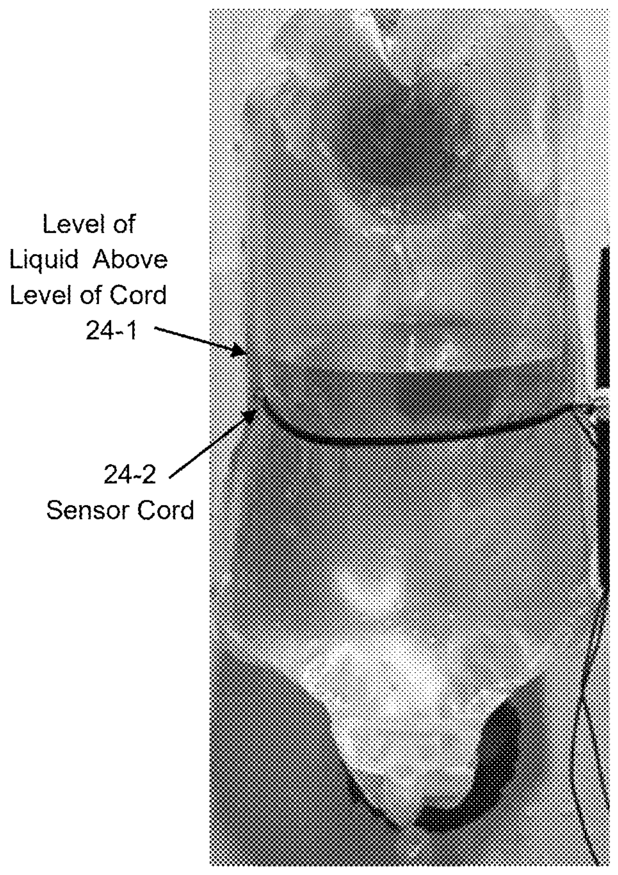
FIG. 24 is a photograph showing a urostomy bag filled to above level of stretch cord sensor.
Figure 25:
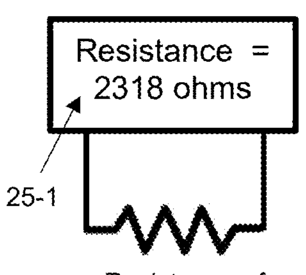
FIG. 25 is an illustration showing the resistance of a cord sensor corresponding to fill level shown in FIG. 24.

If the liquid continues to flow into the bag, rising above the level of the stretch cord sensor, as shown in FIG. 24 at 24-1 and 24-2, the cord continues to stretch, and the cord's resistance continues to increase, in this example from 2015 to 2318 ohms as shown in FIG. 25 at 25-1.

Figures 26A, 26B, 27, 28:
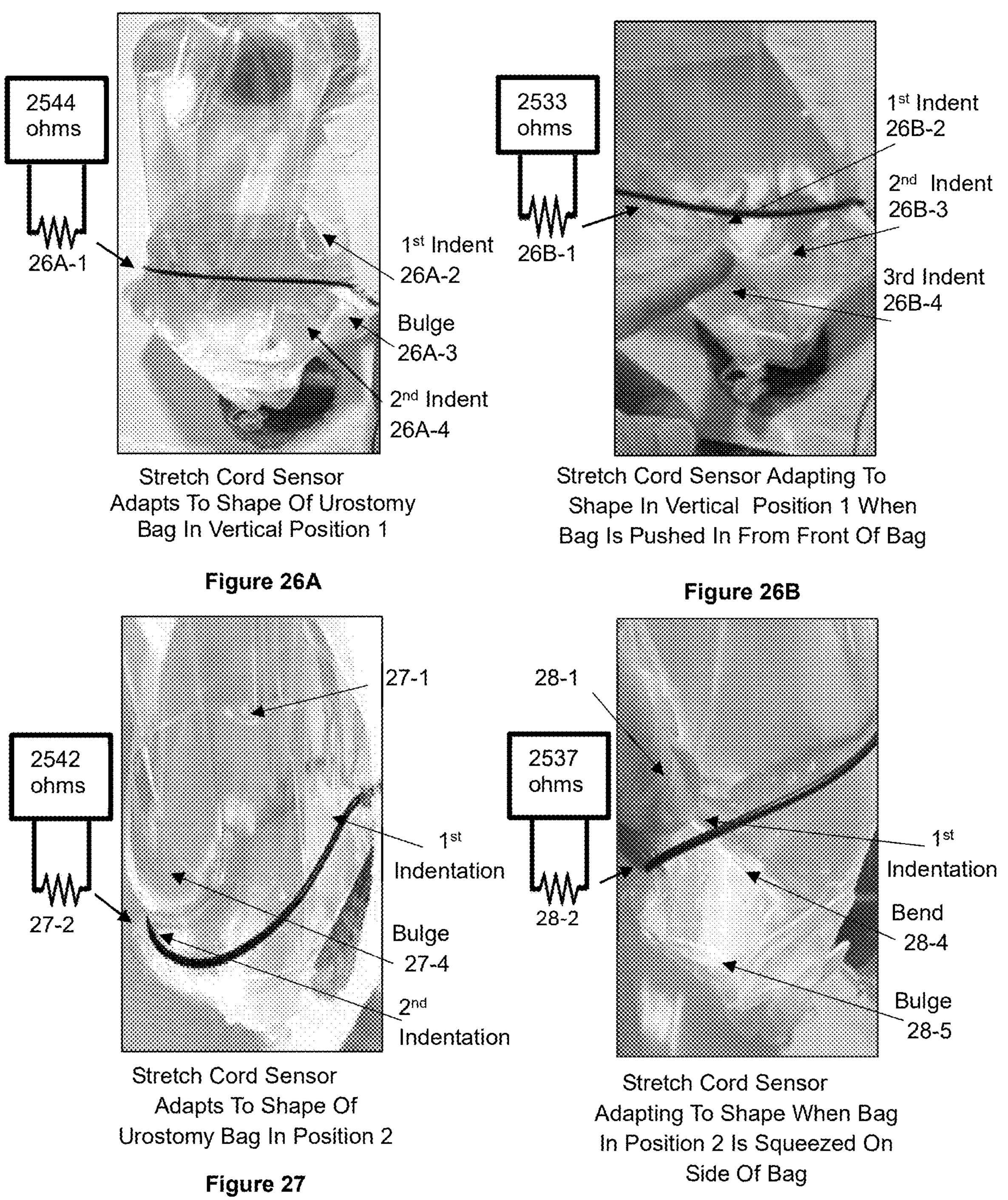
FIG. 26A is a photograph showing that a stretch cord sensor adapts to the shape of a urostomy bag in vertical position 1.
FIG. 26B is a photograph showing a stretch cord sensor adapting to the shape of a bag in vertical position 1 when the bag is pushed in from front of bag.
FIG. 27 is a photograph showing that a stretch cord sensor adapts to the shape of a urostomy bag in vertical position 2.
FIG. 28 is a photograph showing a stretch cord sensor adapting to the shape of a bag in vertical position 2 when the bag is squeezed on the side of the bag.

FIGS. 26A, 26B, 27 and 28 show examples of the stretch cord sensor adapting to changes in the bag's shape. For example, the urostomy bag in FIG. 26A is positioned vertically with a stretch cord sensor resistance equal to 2544 ohms at 26A-1. If the bag is pushed in by a finger as illustrated in FIG. 26B at 26B-2, the stretch sensor adapts to the new shape of the bag. The new shape has a first indentation below the finger at 26B-2, a bend at 28-4, and a second indentation at 26A-4. Even though the shape of the bag changes significantly, the ability of the sensor to adapt to the new shape results in a minimal change in sensor resistance of only 0.4 percent [2544–2533)/2533] as illustrated by the measured resistance value of 2544 ohms at 26A-1 and 2533 ohms at 26B-1.

As another example, the urostomy bag in FIG. 27 at 27-1 has a sensor with a resistance of 2542 ohm at 27-2. If the bag is squeezed as shown in FIG. 28 at 28-1, this changes the shape of the bag and causes the liquid to redistribute within the bag. The new shape has a first indentation at 28-3, a bend at 28-4, and a bulge at 28-5. In response, the stretch cord sensor adapts to the new shape of the bag while only changing sensor resistance from 2542 ohms at 27-2 to 2537 ohm at 28-2 representing a change of less than 0.2% [(2542–2537)/2537]. Such squeezing can occur if the bag is placed into a pouch or if a person bends forward or to the right or left. Such changes in shape would not be tolerated by the hinge detection mechanism described by Stalmann, in Australian Application AU 2021105360 A4.

Figure 29:
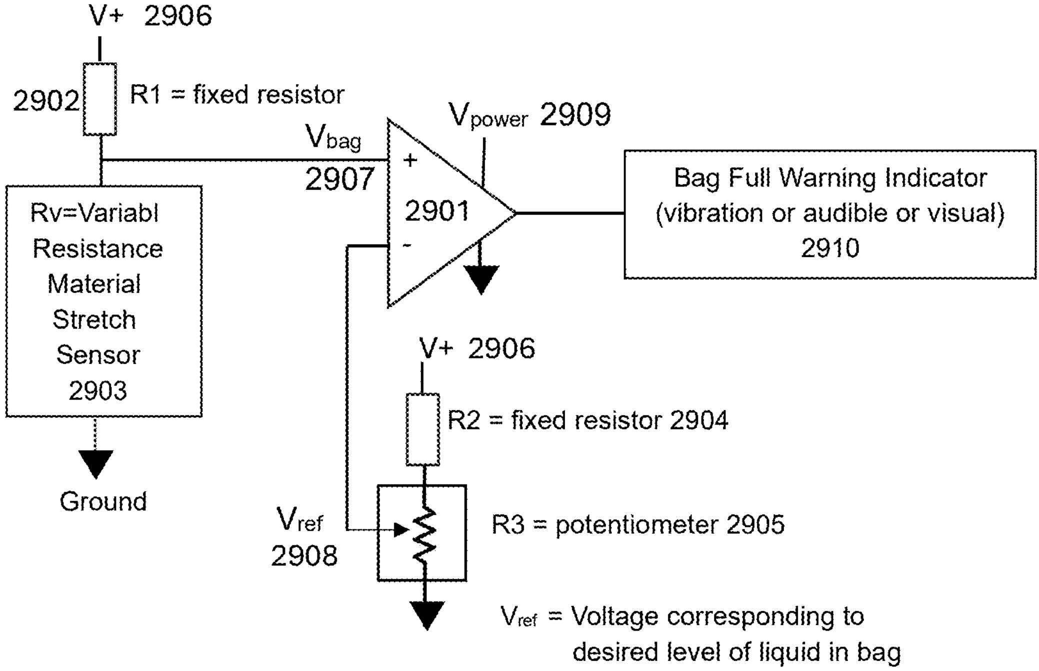
FIG. 29 is a circuit diagram for a warning device.

Once the electrical resistance of the cord indicates that the bag has approximately reached or exceeded a desired fill level, a warning signal is generated to indicate that the bag should be emptied. FIG. 29 is an example of an electrical schematic for such a warning device. The circuit consists of a voltage comparator at 2901, such as an LM339, a fixed resistor R1 at 2902, a stretchable variable resistance material (resistive stretch sensor) wrapped around the bag at 2903, such as resistive rubber cord part number 519 manufactured by Adafruit Industries, a fixed resistor R2 at 2904, potentiometer R3 at 2905, voltage source V+ at 2906, a power source for the comparator $V_{power}$ at 2909, and a "bag full" warning indicator at 2910. $V_{power}$ and V+ can be the same or different voltages.

As the bag fills with liquid (urine), the volume in the bag increases and eventually the sensor material (cord), wrapped around the bag stretches, as shown in FIGS. 16A, 18,22,24. Stretching increases the sensor's resistance Rv at 2903 which increases voltage $V_{bag}$ at 2907 given by:

$$V_{bag} = V + \frac{Rv}{R1 + Rv}$$

When $V_{bag}$ exceeds reference voltage $V_{ref}$ at 2908, voltage comparator 2901 activates the Bag Full Warning Indicator 2910, which can be a vibration device (such as a vibrator), audible device (such as a buzzer), or visual device (such as an LED), or a combination thereof. Reference voltage $V_{ref}$, can be adjusted by potentiometer R3 at 2905, to set the approximate liquid level in the bag at which the Bag Full Warning Indicator 2910 is activated. Full Bag Warning Indicator 2010 is activated when $V_{bag}>V_{ref}$ The present invention works with all types of ostomy bags including urostomy bags with a reflux valve, also referred to as an anti-reflux or back flow protection valve or flap. Such valves are incorporated to prevent urine collected in the bag from flowing back into the human body (stroma). As the bag fills with urine, air in the bag is forced to the top of the bag. The air acts like a buffer cushion between the urine and the valve situated inside the bag in front of fill port in FIG. 30A at 30A-2. The valve is clear, so it is difficult to see in the photograph. When the bag reaches its maximum holding capacity, as determined by the manufacturer, air pressurized from the liquid urine keeps the valve closed preventing any additional urine from flowing into the bag as well as preventing any urine in the bag from flowing back through the stoma into the body. This pressurized air in combination with the volume of liquid in the bag keeps the bag expanded, the resistive cord sensor stretched, and cord resistance high when the bag is in the vertical, tilted, and almost horizontal position, as shown in FIG. 30A at 30A-1, FIG. 31A at 31A-1, and FIG. 32A at 32A-1, corresponding to sensor resistance values of 2166 ohms at 30B-1 (FIG. 30B), 2207 ohms at 31B-1 (FIG. 31B), and 2197 ohms at 32B-1 (FIG. 32B).

In practice, the full bag warning signal should always be set to activate before the bag reaches its maximum capacity and the reflux valve closes. In this example, this would correspond to activating the warning signal before the sensor reaches a resistance value of 2166 ohms, which is the lowest of the resistance values indicated in FIGS. 30A, 31A, and 32A.

Figure 33A:
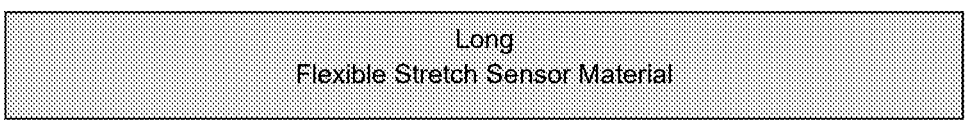
FIG. 33A is an illustration of a long stretch sensor.
Figure 33B:
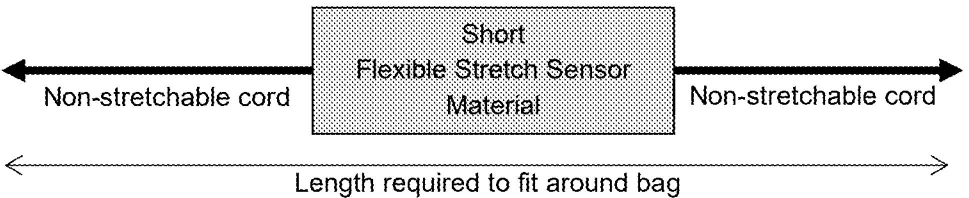
FIG. 33B is an illustration of a short stretch sensor with non-stretch cords

In all the examples of stretch sensors provide thus far, the length of the stretchable material was sufficiently long to wrap around the entire urostomy bag. Such a sensor is illustrated in FIG. 33A. In cases when the stretch sensor material is too short to fit around an entire bag, it can still be used for this application by attaching the shorter stretch sensor to non-stretchable cords on each end of the sensor, as illustrated in FIG. 33B. This enables the shorter sensor to be wrapped around the entire ostomy bag. The combined length (short stretch sensor plus non-stretchable cords) must be less than the perimeter of the bag to ensure that the short stretch sensor is stretched when the bag fills up with fluid. For the purposes of this invention, a stretch sensor is defined as the total length of the short stretch sensor plus the non-stretchable cords attached to it, as illustrated in FIG. 33B. Therefore, either the sensor shown in FIG. 33A or 33B can be used to implement a full bag warning device.

Figure 34:
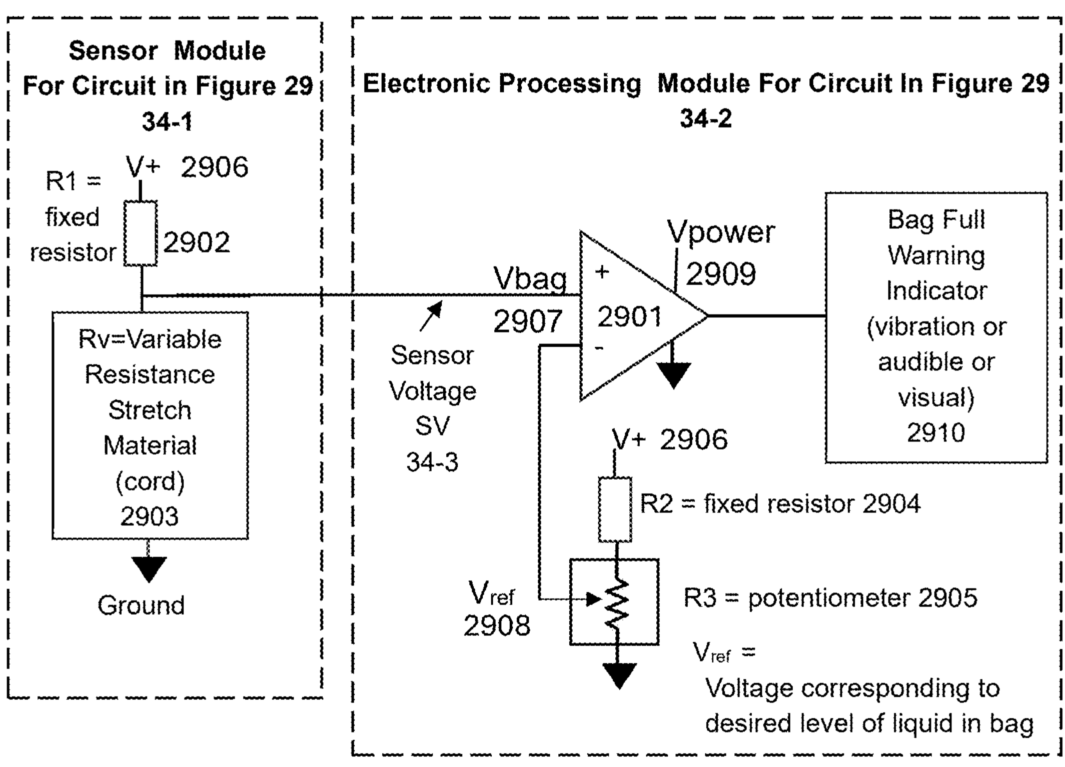
FIG. 34 is a block diagram for a sensor module and electronic processing module for a resistive stretch sensor.

Such stretch sensors are incorporated into the full bag warning circuit shown in FIG. 34 at 2903. FIG. 34 is composed of two separate modules, a sensor module indicated at 34-1, and an electronic processing module indicated at 34-2. The change in stretch sensor resistance, as the sensor is stretched, is converted into a Sensor Voltage referred to as SV at 34-3.

Figure 35:
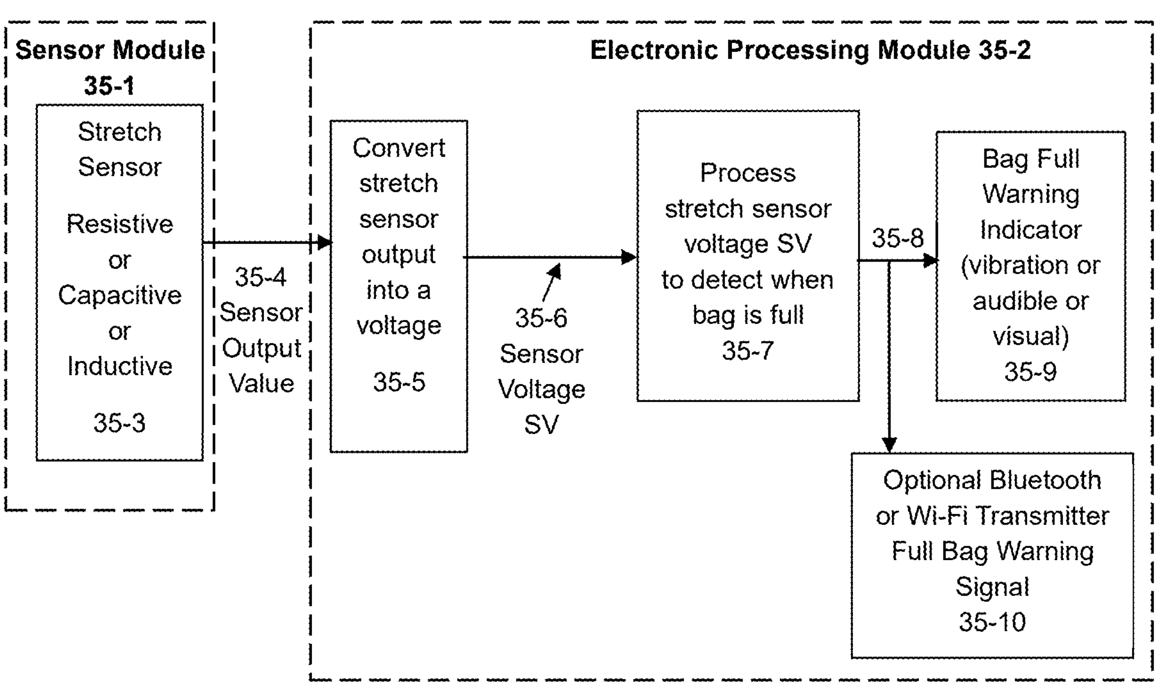
FIG. 35 is a block diagram for a sensor module and electronic processing module for any type of stretch sensor.

In all examples of stretch sensors provided thus far, the electrical resistance changed as the material was stretched. There are other types of stretch sensor materials that can also be used for this application that change either their capacitance or inductance value as they are stretched. FIG. 35 is a generic block diagram for a full bag sensor. It is composed of a sensor module at 35-1 and an electronic processing module at 35-2. Sensor module 35-1 contains at least one resistive, or capacitive, or inductive stretch sensor, at 35-3, that changes its output value, at 35-4, as the sensor is stretched. This change in value is converted by conversion module 35-5 into a voltage SV at 35-6. Voltage SV is processed at 35-7 to detect when the bag is full and generate a warning signal at 35-8 to either trigger a full bag vibration, audible, or visual warning indicator at 35-9, or optionally transmit a signal to a remote device such as a cell phone using a Bluetooth or Wi-Fi transmitter at 35-10, or transmit a signal to a remote location, such as a nurse's station in a hospital or nursing home (or similar attendant's station), also at 35-10, to indicate that the bag needs to be emptied or replaced.

Figure 36:
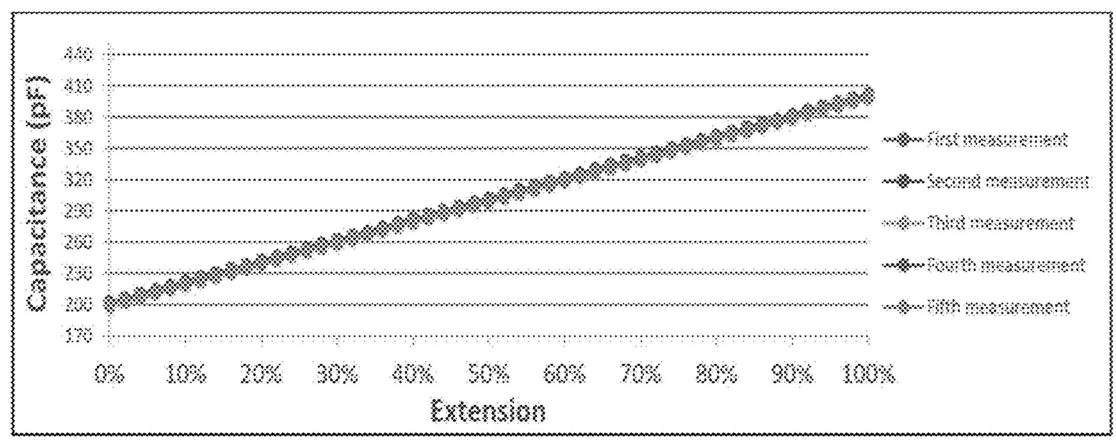
FIG. 36 is a graph from a manufacturer's datasheet showing the change in capacitance value as a function of extension for Alpha part number EC100-N-421-AO1.

As indicated in FIG. 35 at 35-3 the stretch sensor can be a stretchable material whose resistance, capacitance, or inductance changes as the sensor is stretched. One example of a capacitive stretch sensor is part number EC100-N-421-AO1 manufactured by Alpha. FIG. 36 from the manufacturer's datasheet shows the change in capacitance value as the sensor is stretched.

When using such a capacitive stretch sensor to detect bag expansion, there are multiple methods that can be used in FIG. 35 at 35-5 to convert the change in capacitance at 35-4 to voltage SV at 35-6. One example consists of the following three steps:

Step 1: Use the capacitive stretch sensor as the capacitor in an oscillator circuit: An oscillator circuit, such as a 555 timer or a relaxation oscillator, has a frequency of oscillation that depends on the capacitance in the 555 timer circuit.

Step 2: The capacitive value of the sensor changes as the sensor is stretched: As the sensor's capacitance changes, the oscillator's frequency will change accordingly.

Step 3: Convert frequency to voltage: A frequency-to-voltage converter IC, for example an LM 2907 manufactured by Texas instruments, or a simple filter circuit can be used convert this variable frequency into a corresponding DC voltage SV at 35-6.

Alternatively, as also indicated in FIG. 35 at 35-3, the stretch sensor can be a stretchable material whose inductance changes as the sensor is stretched. For example, companies by the name of Amhor and Soft Robotics Tool Kit both manufacture inductive stretch sensors. When an inductive stretch sensor is used at 35-3, the output of the sensor at 35-4 is converted at 35-5 to produce a voltage SV at 35-6.

In addition to using different types of stretch sensors (resistive, capacitive, or inductive) to detect that the bag is filling with liquid, there are alternative sensor bag attachment configurations that do not require wrapping the sensor around the entire bag.

However, common to all configurations of this invention is that the linear length of bag material covered by the stretch sensor must be greater than the length of the sensor, when the sensor is not stretched, as illustrated in FIGS. 37A through 37E, such that when the bag fills to the desired fill level, the bag exerts a force onto the sensor, stretching the sensor and changing the sensor's resistance, capacitance, or inductance. In response to this force, the stretch sensor produces a countervailing force onto the bag which is equal to and opposite to the force exerted by the bag.

FIG. 37A shows a stretch sensor at 37A-1 wrapped around the entire urostomy bag. FIG. 37B shows the stretch sensor at 37B-1 attached to only one side of the bag (either front or back) with two fixed attachment points at 37B-2 and 37B-3 located at the right and left sides of the bag. FIG. 37C shows the stretch sensor at 37C-1 also attached to only one side of the bag (either front or back) but with the distance between the two fixed attachment points at 37C-2 and 37C-3 being less than the distance between the right and left sides of the bag. FIGS. 37A, 37B and 37C also include top cross section slice views for each different attachment configuration.

FIG. 37A at 37A-1 shows the stretch sensor wrapping around the entire bag with the perimeter of the bag being greater than the perimeter of the sensor, when the sensor is not stretched. Thus, the bag when empty must be folded or collapsed to fit within the smaller perimeter of the unstretched sensor as illustrated at 37A-1, 37A-2, 37A-3. This ensures that when the bag fills to the desired fill level, the filled bag unfolds applying pressure to the sensor and stretching the sensor to change its resistance, capacitance, or inductance.

FIG. 37B at 37B-1 and 37C at 37C-1 show the stretch sensor only covering a section of the bag's perimeter located on one side of the bag. FIG. 37B shows the linear length of the bag LB at 37B-9, when the bag is empty and collapsed, with the bag folded inward as illustrated at 37B-6. This section of the bag is collapsed at 37B-7 and is covered by the sensor, which is not stretched. The length of the sensor when not stretched is LS as indicated at 37B-10, such that LS<LB. When the bag fills to the desired fill level, the filled bag unfolds and applies pressure to the sensor which stretches the sensor and changes the sensor's resistance, capacitance, or inductance.

Regions that are collapsed when the bag is empty are shown for each configuration in FIG. 37 at 37A-2, 37A-3, 37B-6, 37B-7 and 37C-6, 37C-7. When the stretch sensor is wrapped around the bag, as illustrated at 37A-1 and 37D-1, the perimeter (circumference) of the folded bag material covered by the sensor at 37D-2 is greater than the perimeter (circumference) of the unstretched sensor at 37A-1 and 37D-1, when the bag is empty, to satisfy the condition that LS<LB. For configurations in which the stretch sensor is only attached to one side of the bag, the top cross slice views indicate the fixed sensor attachment points at 37B-4, 37B-5, and 37C-4, 37C-5, with corresponding sensor mounting posts shown at 37B-11, 37B-12 and 37C-8, 37C-9. In FIG. 37A the stretch sensor at 37A-1 is wrapped around the entire bag. The cord stretch sensor at 37A-4 freely slides within bag mounting posts 37A-5 and 37A-6. Multiple mounting posts can be used to hold the sensor around the bag without influencing sensor performance because the cord freely slides through each post. FIG. 37A illustrates two different types of mounting posts. The post at 37A-5 fully encapsulates the cord stretch sensor, while the post at 37A-6 has an opening at 37A-7 with a retention springing action to permit easy installation and removal of the cord stretch sensor and to prevent it from falling out of the mounting post once inserted. Each mounting post can be attached to the bag, as illustrated at 37A-8, by using an adhesive glue to bond the post to the bag.

FIGS. 37D and 37E show countervailing forces produced by the stretch sensor for the different mounting configurations shown in FIGS. 37A, 37B and 37C. FIG. 37D shows stretch sensor 37D-1 wrapped around ostomy bag 37D-2. When the bag is empty, the sensor is not stretched. This enables the perimeter of the flaccid bag, which must be greater than the perimeter of the unstretched sensor, to be folded or collapsed, as shown at 37D-3 and 37D-4, so that the bag can be fit into the smaller perimeter of the sensor. It is important to emphasize that the perimeter of the bag is constant. It cannot change because it is manufactured with a fixed amount of material that does not stretch.

When the bag fills with urine or waste product to a predetermined level, the walls of the bag begin to push into and exert an outward force B at 37D-4 onto the sensor. In response to force B, the sensor stretches to exert an equal and opposite countervailing force S at 37D-5 so that the bag and urine or waste products always remain in a state of equilibrium. This is achieved without attaching any additional reference surfaces to the stretch sensor. As the sensor stretches it changes its resistance, capacitance, or inductance value.

FIG. 37E shows the stretch sensor 37E-1, with a length LS, only covering a portion of the bag's perimeter, on the front or rear surface of the bag. When the bag is empty and the sensor is not stretched, the length of the collapsed bag, LB, covered by the sensor at 37E-3, is greater than the length of the unstretched sensor LS. When the bag fills with urine or waste product to a predetermined level, the walls of the bag begin to push and exert an outward force B at 37E-4 onto the sensor, In response to force B, the sensor stretches to exert an equal and opposite countervailing force S at 37E-5 and 37E-6 so that the bag and urine or waste product always remain in a state of equilibrium. This is achieved without attaching any additional reference surfaces to the stretch sensor. As the sensor stretches it changes its resistance, capacitance, or inductance value.

Of the three configurations shown in FIGS. 37A, 37B and 37C, wrapping the stretch sensor around the entire bag as illustrated in FIGS. 37A and 37D, has advantages over the configurations illustrated in FIGS. 37B, 37C and 37E.

A first advantage is that ostomy bags are mass produced by multiple companies such as, for example Convatec, Hollister and Coloplast, with each maintaining their dimensions to tight manufacturing tolerances. This enables wrap-around stretch sensors to be prefabricated such that they are optimized for each different manufacturer's bag. Optimization means that the length of the wrap-around stretch sensor, which may include a non-stretchable cord, as shown in FIGS. 33A and 33B, can be manufactured to stretch a predetermined amount when the level of liquid in the bag reaches a predetermined percentage of the bag's recommended capacity as illustrated by comparing FIGS. 16A, 16B, 18, 22, 23, 24, 25.

A second advantage is that the wrap-around stretch sensor can be easily placed into and removed from inexpensive adhesively mounted disposable posts mounted to the bag, as illustrated in FIG. 37A at 37A-6, to provide easy installation, removal, and reuse of the stretch sensor. This is extremely important to patients, because most patients typically use more than 100 urostomy bags per year. Easy installation and reuse is made possible because there are no critical sensor installation or assembly adjustments required to install or remove the wrap-around stretch sensor from the bag.

In comparison, the sensor configurations and attachment methods illustrated in FIGS. 37B and 37C, both require critical alignment of the stretch sensor relative to the bag. In both configurations (FIGS. 37B and 37C), the fluid level at which the sensor begins to stretch is a function of both the distance between the sensor attachment posts, at 37B-11, 37B-12 or 37C-8, 37C-9, and the amount of collapsed bag material covered by the unstretched sensor at 37B-7 or 37C-7, all of which are subject to human error when the sensor is attached to the bag. While attaching the sensor to the sides of the bag, as shown in FIG. 37B is less prone to error than the configuration shown in FIG. 37C, both methods of installation are subject to human error, and if either of these mounting configurations are to be implemented, they are best performed as part of the manufacturing process with the stretch senor being preinstalled by the bag manufacturer.

Another important factor influencing bag performance is the weight of the sensor and its interaction with the reflux value designed to prevent urine and bacteria from flowing out of the bag and back through the stoma into the body. These reflux valves are designed by the manufacturer to close when air pressurized by a high fluid level in the bag reaches and exceeds a predetermined manufacturer's threshold. FIGS. 30A, 31A, and 32A show how the pressurized air in a full bag keeps the reflux valve closed and bag expanded in various bag positions, when the urostomy bag is at maximum capacity. Any excessive weight or force applied to the surface of the bag by a sensor will increase internal bag pressure which could cause the reflux valve to close prematurely and limit the amount of fluid that the bag can hold.

A major advantage of using a stretchable carbon impregnated variable resistive rubber cord as the sensor is its small size and light weight. For example, the rubber cord stretch sensor used in FIGS. 16A through 32A (part number 519 manufactured by Adafruit Industries) is only 2 mm (0.078 inches) in diameter, 228.6 mm (9.0 inches) in length and only weights approximately 0.65 grams (0.02 ounces) which does not in any way influence the functionality of the reflux valve, as illustrated in FIGS. 30A, 31A, and 32A.

Another advantage of using a rubber cord stretch sensor is that the rubber material is not damaged should it become exposed to urine or other such body fluids or water during patient showers.

Figure 38:
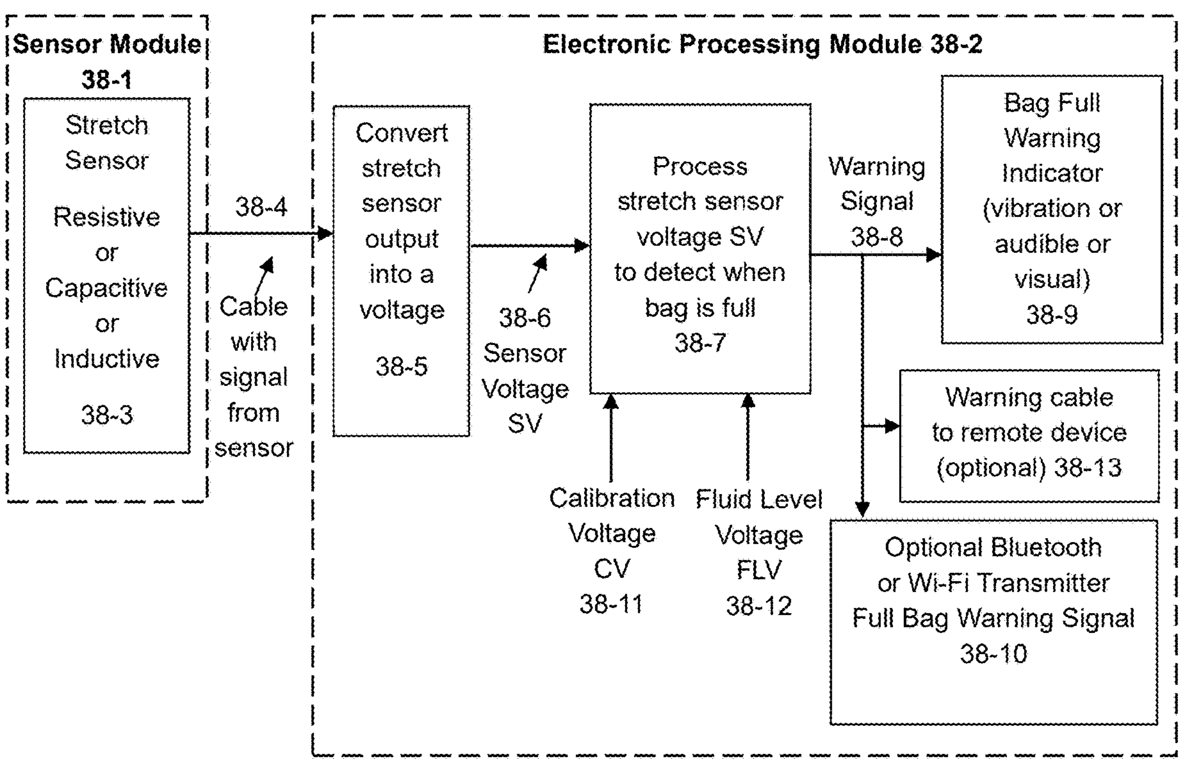
FIG. 38 is a block diagram for a sensor module and electronic processing module with calibration and fluid level adjustments.
Figure 42A:
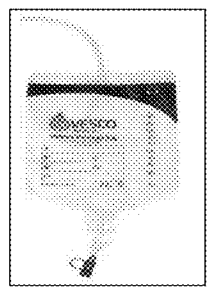
FIGS. 42A through 42E are photographs showing types of drainage bags by different manufacturers.
Figure 42B:
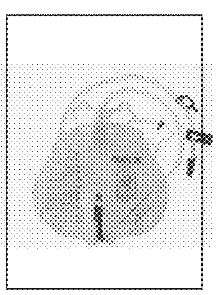
Figure 42C:
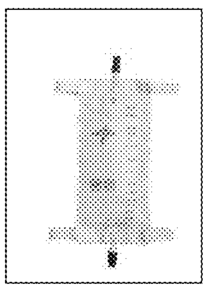
Figure 42D:
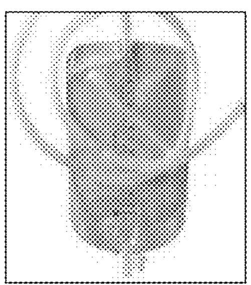
Figure 42E:
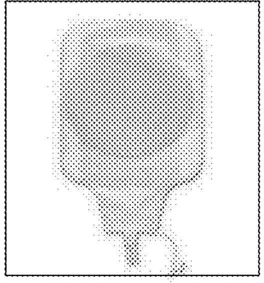

In the event that the rubber cord stretch sensor or any other type of stretch sensor needs to be replaced, a sensor calibration feature is incorporated into the electronic processing module to adjust for differences in sensor voltage SV between different sensors. This added calibration voltage, referred to as CV, is indicated in FIG. 38 at 38-11 and corresponds to sensor voltage SV produced at 38-6 when the sensor is not stretched, such as when the bag is empty. The fluid level at which the warning signal at 38-9 is activated is separately controlled by newly added fluid level voltage FLV indicated at 38-12. FLV corresponds to the amount that sensor voltage SV at 38-6 changes between when the sensor is not stretched and when it is stretched to the fluid level at which the warning signal is to be activated.

Having separate controls enables the bag user to recalibrate the electronics for a new or replaced sensor without having to readjust voltage FLV that sets the fluid level at which the warning alarm is activated.

To make it even easier for the user, the manufacturer could sell urostomy bags with preinstalled sensors such that the user would only need to connect a cable between the stretch sensor on the newly purchased bag and its electronic processing module, thereby eliminating the entire sensor/bag mounting procedure.

Manufacturing such sensor preinstalled bags is greatly facilitated by the low cost and simplicity of using a simple rubber cord sensor or any other low cost sensor made of a different lightweight stretchable material. FIGS. 39A, 39B, and 39C illustrate various stretch sensor configurations preinstalled on a bag by the manufacturer using mounting posts at 39A-2, 39B-2 and 39C-2. FIGS. 40A, 40B, and 40C illustrate various stretch sensor configurations preinstalled on a bag by the manufacturer in which the stretch cord sensor is placed into a continuous channel or channel sections integrated into the bag structure as shown at 40A-2, 40B-2, and 40C-2.

While the previous examples describing this invention were illustrated using a urostomy bag, this invention is intended for use with all types of ostomy bags (urostomy, colostomy, and ileostomy).

As previously explained, ostomy products are designed for three types of stomas: colostomies, ileostomies, and urostomies. Colostomies are formed from the large intestine, and the output is often thicker or even formed stool. Ileostomies are formed from the lowest part of the small intestine, and the output is liquid stool which can sometimes be more frequent than a colostomy. The final type of ostomy is a urostomy, which is done when the bladder must be removed or bypassed due to injury or disease. Urostomy output consists of urine and mucus.

FIGS. 41A through 41I show pictures of the three types of ostomy bags, colostomy, ileostomy, and urostomy, manufactured by three different manufacturers, Coloplast, Hollister and Convatec. Reflux is not a concern after colostomy or ileostomy procedures, so these bags typically do not require or have reflux valves. Common to all the colostomy, ileostomy and urostomy bags shown in FIGS. 41A through 41I is that they are all flaccid, flexible foldable bags with a fill port toward the top of the bag. This enables the full bag warning device, illustrated in FIG. 38, to be used with all three types of ostomy bag products (colostomy, ileostomy, urostomy) to detect when the bags are full and need to be emptied or replaced. As reference, the urostomy bag shown in FIG. 41H manufactured by Convatec is used in FIGS. 16 through 32A to describe how this invention works.

Other uses for this invention include monitoring fluid levels in drainage bags. When attached to the body through a catheter, flexible foldable drainage bags with fill ports are frequently used to collect bodily waste and excretions from healing wounds. These drainage bags are frequently found attached to patients in hospital beds, wheelchairs, at home recovering from surgery, or even attached to a patient's leg as they walk around for greater capacity.

FIGS. 42A through 42E are images of commercially manufactured bodily fluid and wound drainage bags. Common to all the drainage bags shown is that they are all flexible foldable bags with a fill port toward the top of the bag. This enables the full bag warning device described in this invention to be used with all these drainage bags, to detect when such bags are full and need to be emptied or replaced.

For patients in a hospital bed, or nursing home, the full bag warning device can be connected to a centrally located attendant's station to to indicate that a patient's bag needs to be serviced.

It is important to emphasize that the purpose of this invention is not to provide a precise measurement of waste volume in an ostomy bag or drainage bag but instead to provide an early warning signal that the bag is approaching its full level and to make provisions to empty the bag before it becomes too full.

For example, assume that the full bag warning signal in FIG. 38 at 38-8 and warning indicator at 38-9 or 38-10 or 38-13, are set to activate when the ostomy or drainage bag is approximately 75% full but, due to variations in bag position (if the person is standing or sitting) and sensor repeatability, the bag full indicator activates anywhere between seventy percent (70%) and eighty percent (80%) of full bag capacity. This degree of variation is acceptable for these applications and achieves the goal of informing the patient or attendant that the bag is approaching maximum capacity and to begin making preparations to empty or replace the bag.

Another use for this invention is to monitor fluid levels in bags dispensing medication or blood and to produce a warning signal when fluid levels are almost empty. When prefilled with blood or medication in liquid form, flexible foldable bags connected to a patient through an IV line are frequently used to administer its contents to a patient. FIGS. 43A and 43B are examples of such bags filled with human blood. FIGS. 44A, 44B, and 44C are example of such a bag, manufactured by Mckesson, filled with sodium chloride. To indicate when such bags are almost empty, a stretch sensor is placed at a predetermined position on the bag as indicated in FIG. 44 at 44B-1. When the contents of the bag is sufficiently above a predetermined level, such that the sensor is stretched, the sensor processing electronics is adjusted to indicate that the bag fluid level is higher than the predetermined level. When the bag fluid level falls sufficiently below the predetermined level of the sensor, such that the sensor is no longer stretched, or stretched to a lesser degree, the change in sensor value is processed to indicate that the bag is almost empty.

In FIGS. 45A and 45B, a bag design is proposed in which the lowest part of the bag has a funnel shape with a smaller diameter and or perimeter than the section above it. As the bag empties, the change in vertical fluid height per volume of fluid released from the bag will be greater in the narrow lower section than in the wider upper section. Wrapping a stretch sensor around the bag toward the top of the narrow section, as illustrated at 45A-1 and 45B-1, facilitates detecting changes in vertical fluid level at 45A-2 and 45B-2 before the bag is totally empty. Multiple stretch sensors can be attached to a bag to indicate when the fluid level drops below certain predetermined vertical heights. For example, the bag in FIG. 44C has three stretch sensors located at 44C-1, 44C-2, 44C-3 to detect when the bag fluid level is low, half full, or high respectively. In FIG. 45A, the bag has two stretch sensors, a half full fluid level sensor at 45A-3 and a Bag Almost Empty sensor at 45A-1.

Furthermore, for ease of use, sensors can be preinstalled by the manufacturer at a height on the bag predetermined by the manufacturer to indicate when the bag is half full or almost empty. For example, the stretch sensors shown in FIG. 45A at 45A-3 and 45A-1 can be installed into channels integrated into the bag by the manufacturer at 45A-4 and 45A-5 respectively. In FIG. 45B at 45B-1, the almost empty sensor at 45B-1 can be preinstalled by the manufacturer into a channel integrated into the bag at 45B-3.

FIGS. 46A, 46B, and 46C show different stretch sensor mounting configurations using posts to mount the sensor onto the exterior surface of a medication or blood IV bag. FIG. 46A shows the stretch sensor wrapping around the entire medication or blood IV bag using mounting posts to attach the sensor to the IV bag at 46A-2, 46A-3. FIGS. 46B and 46C shows the sensor mounted to only one surface of the IV bag using mounting posts at 46B-2, 46B-3, and 46C-2, 46C-3 respectively.

FIGS. 47A, 47B, and 47C show different stretch sensor mounting configurations with the sensor preinstalled by the manufacturer into a channel or channels integrated into the medication or blood IV bag. FIG. 47A shows the stretch sensor wrapping around the entire medication or blood IV bag installed into a channel at 47A-2. FIGS. 47B and 47C shows the stretch sensor mounted to only one surface of the IV bag, installed into channels on one side of the bag, located at 47B-4 and 47C-4.

FIG. 48 is a block diagram for a circuit to support the three stretch sensors illustrated in FIG. 44 at 44-C1, 44-C2 and 44C-3, respectively. If only two stretch sensors are used, as illustrated in FIG. 45A at 45A-2 and 45A-3, modules 48-SM-3 and 48-EPM-3 to support the third sensor can be eliminated. If only one sensor is used, as illustrated in FIG. 45B at 45B-1, module 48-SM-2 and 48-EPM-2 that supports the second sensor can be eliminated. In FIGS. 48 and 38, module 48-7 and 38-7, respectively, can either be implemented using discrete components such as, for example voltage comparator 2901 in FIG. 29, or using a microprocessor, such as for example an Atiny24/44/88 manufactured by Microchip technology.

Another major feature of this invention, which is extremely important for medical products such as bags containing blood, sodium chloride, antibiotics, pain medication, etc., is that the sensors in this invention never make contact with the sterile contents within the bag.

It is important to emphasize that the purpose of this invention for bags dispensing blood or medication is not to provide a precise measurement of liquid volume in the IV bag, but instead to provide an early warning signal that the bag is approximately below a predetermined position or almost empty, and if almost empty to make provisions to replace the bag while there is still a small amount of blood or medication remaining.

Likewise, for ostomy and drainage bags, the purpose of this invention is not to provide a precise measurement of waste product in the bag, but instead to provide an early warning signal that the bag is almost full and to make provisions to empty or replace the bag before it reaches maximum capacity.

CONCLUSION

To summarize, this invention describes a warning device to check if an ostomy, drainage, or wound bag is full and needs to be emptied or if an IV bag dispensing medication or blood is empty and needs to be replaced.

The warning device incorporates a unique stretch sensor that adapts to the shape of the filled bag. The sensor can be easily attached to the outside of bags currently in commercial production or integrated by a manufacturer onto a bag and the stretch sensor does not require any additional countervailing force or external reference surface. An electronic module attached to the sensor can be programmed to produce a warning signal when the ostomy or drainage bag is almost full or when a bag dispensing medication is below a predetermined level or is almost empty.

The foregoing description of example embodiments illustrates and describes devices and methods for implementing a warning device to check if an ostomy, drainage, or wound bag is full and needs to be emptied or if an IV bag dispensing medication or blood is empty and needs to be replaced, but is not intended to be exhaustive or to limited to the precise form disclosed.

Certain portions may be implemented as "logic" that performs one or more functions. This logic may include hardware, such as hardwired logic, an application-specific integrated circuit, a field programmable gate array, a graphical processing unit, or may also include in whole or in part, a processor that executes software instructions. Some or all of the logic may therefore be stored in one or more tangible non-transitory computer-readable storage media and may include computer-executable instructions that may be executed by a computer, a data processing system, application specific integrated circuit, programmable gate array or any other state machine. The computer-executable instructions may include instructions that implement one or more embodiments described herein.

It also should be understood that the block and process flow diagrams may include more or fewer elements, be arranged differently, or be represented differently. For example, while a series of steps has been described above with respect to the block diagrams, the order of the steps may be modified to achieve the same result. In addition, the steps, operations, and steps may be performed by additional or other hardware or software modules or entities, which may be combined or separated to form other modules or entities. For example, while a series of steps has been described with regard to certain Figures, the order of the steps may be modified in other consistent implementations. Further, nondependent steps may be performed in parallel. Further, disclosed implementations may not be limited to any specific combination of hardware or software.

It is apparent that other variations and modifications may be made to the embodiments described, with the attainment of some or all of their advantages. Therefore, it is the object of the appended claims to cover all such variations and modifications as come within the true spirit and scope of the disclosure herein and their equivalents.

What is claimed is:

1. A warning device for an ostomy, drainage, or wound bag configured to detect when the bag is full and needs to be emptied that does not require the bag or a section thereof to stretch, comprising:

a. a flaccid foldable collapsible bag with a fill port that fills with liquid urine or waste product (FIG. 16A);

b. a sensor, attached to the bag, the sensor composed of a stretchable material that changes either resistance, capacitance, or inductance as the sensor is stretched, with at least a portion of the bag being covered by and free to move relative to at least a portion of the sensor (FIGS. 24,25, 35);

c. the sensor being attached to the bag so that either:

i. the sensor wraps around an entire perimeter of the bag, but with a perimeter of the sensor being smaller than the perimeter of the bag, requiring the bag to be folded and collapsed to fit within the smaller perimeter of the sensor, when the sensor is unstretched (FIG. 37D); or ii. the sensor covers a portion of the bag perimeter, such that when the bag is empty; the sensor is unstretched and the portion of the bag perimeter covered by the unstretched sensor has a linear material length longer than the length of the unstretched sensor, requiring the bag to be folded and collapsed to fit within the space covered by the sensor in its unstretched state (FIG. 37E);

d. such that when the bag is filled to a predetermined level with urine or waste product, the bag pushes and exerts a force onto the sensor thereby changing the resistance, capacitance, or inductance of the sensor without requiring the bag or a section thereof to stretch (FIGS. 18, 19);

e. in response to being stretched, the sensor, without requiring any additional reference surfaces, exerts a countervailing force equal to and opposite to the force exerted onto the sensor by the bag (FIGS. 37D, 37E);

f. as more urine or waste product continues to flow into the bag, increasing bag volume, the bag exerts more force onto the sensor, further changing the resistance, capacitance or inductance of the sensor (FIGS. 24,25); and g. in response, the sensor exerts a stronger countervailing force equal to and opposite to the force exerted onto the sensor by the bag (FIGS. 37D,37E);

h. an electronic processing module connected to the sensor to detect and generate a warning signal when the bag is full or needs to be emptied (FIG. 38); and i. the warning signal being fed to at least one of: a warning indicator such as a vibration, audible or visual device, a Bluetooth transmitter, a Wi-Fi transmitter, a warning cable for connection to a remote device, or combinations thereof (FIG. 38).

2. The warning device of claim 1 wherein at least one of the vibration, audible or visual device, Wi-Fi transmitter, or Bluetooth transmitter is worn by a person whom the bag is attached to.

3. The warning device of claim 1 wherein at least one of the warning cable, the Wi-Fi transmitter, or the Bluetooth transmitter is connected to a remote device located at an attendant's station to indicate when the bag is full and needs to be emptied.

4. The warning device of claim 1 wherein the sensor is attached to an exterior of the bag using mounting posts (FIGS. 37C, 39B).

5. The warning device of claim 1 wherein the sensor is pre-installed by a bag manufacturer into channels integrated into the bag (FIG. 40).

6. The warning device of claim 1 wherein the sensor is a stretchable carbon impregnated rubber cord whose electrical resistance changes as the cord is stretched (FIG. 16A).

7. An ostomy, drainage, or wound bag warning device to detect when a bag is full and needs to be emptied without requiring the bag or a section thereof to stretch, comprising:

- a. a flaccid, flexible, foldable collapsible bag with a fill port that fills with liquid urine or waste product (FIG. 16A);
- b. a sensor, attached to the bag, the sensor composed of a stretchable material that changes either resistance, capacitance, or inductance as the sensor is stretched with at least a portion of the bag being covered by, and free to move relative to at least a portion of the sensor (FIGS. 24, 25, 35);
- c. the sensor further being attached to the bag so that either:
  - i. the sensor wraps around an entire perimeter of the bag, but with a perimeter of the sensor being smaller than the perimeter of the bag, requiring the bag to be folded and collapsed to fit within the smaller perimeter of the sensor when the sensor is unstretched (FIG. 37D); or
  - ii. the sensor covers a portion of the bag perimeter, such that when the bag is empty; the sensor is unstretched and the portion of the bag perimeter covered by the unstretched sensor has a linear material length longer than the length of the unstretched sensor, requiring the bag to be folded and collapsed to fit within the space covered by the sensor in its unstretched state (FIG. 37E);
- d. as the bag fills with waste product, a shape of the bag changes such that at a predetermined level of waste product in the bag, the bag begins to put force onto the sensor, and in response thereto, the sensor changes its shape by stretching to adapt to the shape of the bag, the sensor covering a sufficient portion of the bags perimeter such that as the contents of the bag redistributes within the bag in response to a person changing position, the sensor remains stretched, without requiring the bag to stretch (FIGS. 21B, 28);
- e. the resulting stretching also changing the resistance, capacitance, or inductance of the sensor;
- f. as urine or waste product continues to flow into the bag, the sensor continues to stretch changing its resistance, capacitance or inductance as the sensor continues to adapt to the changing shape of the bag (FIGS. 22 through 25);
- g. the sensor also adapts to changes in the shape of the bag, due to the bag being bent, twisted, tilted, or squeezed (FIGS. 20, 21A, 21B, 28);
- h. an electronic processing module connected to the sensor to detect and generate a warning signal when the bag is full or needs to be emptied (FIG. 38); and
- i. the warning signal being fed to at least one of: a warning indicator such as a vibration, audible or visual device, a Bluetooth transmitter, a Wi-Fi transmitter, a warning cable for connection to a remote device, or combinations thereof (FIG. 38).

8. The warning device of claim 7 wherein at least one of the vibration, audible or visual device, Wi-Fi transmitter, or Bluetooth transmitter is worn by a person whom the bag is attached to.

9. The warning device of claim 7 wherein at least one of the warning cable, the Wi-Fi transmitter, or the Bluetooth transmitter is connected to a remote device located at an attendant's station to indicate when the bag is full and needs to be emptied.

10. The warning device of claim 7 wherein the sensor is a stretchable carbon impregnated rubber cord whose electrical resistance changes as the cord is stretched (FIG. 16A).

11. A warning device for an IV bag dispensing medication or blood to detect when contents of the bag fall below a predetermined level without requiring the bag or a section thereof to stretch, the warning device comprising:

- a. a sensor composed of a stretchable material that changes either resistance, capacitance, or inductance as stretch of the sensor changes (FIGS. 44C, 46);
- b. the sensor further configured to be attached to a flaccid foldable collapsible bag for holding liquid medication or blood with at least a portion of the bag being covered by, and free to move relative to at least a portion of the sensor (FIGS. 43A, 44);

so that either:

- i. the sensor wraps around an entire perimeter of the bag, with a perimeter of the sensor being smaller than the perimeter of the bag, requiring either:
  - A. the bag is folded and collapsed to fit within the smaller perimeter of the sensor when the sensor is unstretched, or
  - B. the sensor is stretched to fit around and cover the entire perimeter of the bag causing at least a portion of the bag to fold or collapse underneath the stretched sensor (FIGS. 45A, 46A); or
- ii. the sensor covers a portion of the bag perimeter, such that when the bag is empty; the sensor is unstretched and the portion of the bag perimeter covered by the unstretched sensor has a linear material length longer than a length of the unstretched sensor, requiring either:
  - A. the bag is collapsed and folded to fit within the space covered by the sensor in its unstretched state, or
  - B. the sensor is stretched to cover a portion of the bag causing the bag to be folded or collapsed underneath the stretched sensor;

so that when the contents in the bag exceed a predetermined level, the bag stretches the sensor and when the contents falls below a predetermined level, the bag no longer stretches the sensor (FIGS. 46B, 47B);

- c. and further such that the sensor is configured to be located on the bag at a predetermined position with respect to a level of medication or blood in the bag to insure that the bag pushes into and exerts forces onto the sensor without requiring the bag or a section thereof to stretch (FIGS. 44B, 45B);

d. in response to being stretched, the sensor, without requiring any additional reference surfaces, exerts a countervailing force equal to and opposite to the force exerted onto the sensor by the bag (FIG. 37D);

e. as medication or blood continues to flow out of the bag, a volume of the bag decreases such that the bag exerts less force onto the sensor;

f. in response thereto, the sensor exerts a weaker countervailing force opposite to the force exerted onto the sensor by the bag, thereby causing the sensor to change its resistance, capacitance or inductance;

g. when contents of the bag drop below a predetermined level, the force exerted by the bag onto the sensor decreases by a predetermined amount indicating the sensor is no longer sufficiently stretched;

h. an electronic processing module, configured to detect a resistance, capacitance or inductance value corresponding to a sensor that is no longer sufficiently stretched, and to generate a warning signal to indicate that the contents of the bag have fallen below the predetermined level (FIG. 48 at 48-7); and h. the warning signal being fed to at least one of a warning indicator such as a vibration, audible or visual device, a Bluetooth transmitter, a Wi-Fi transmitter, or a warning cable for connection to a remote device (FIG. 48).

12. The warning device of claim 11 wherein at least one of the vibration, audible or visual device, Wi-Fi transmitter, or Bluetooth transmitter, or combinations thereof is worn by a person whom the bag is attached to.

13. The warning device of claim 11 wherein at least one of; the warning cable, the Wi-Fi transmitter, or the Bluetooth transmitter is connected to a remote device located at an attendant's station in a hospital or nursing home to indicate when the contents of the bag has fallen below the predetermined level.

14. The warning device of claim 11 wherein the sensor is further configured to be attached to an exterior of the bag using mounting posts (FIG. 46A,46B,46C).

15. The warning device of claim 11 wherein the sensor is pre-installed by a bag manufacturer into channels integrated onto the bag (FIG. 47A,47B,47C).

16. The warning device of claim 11 wherein the sensor is a stretchable carbon impregnated rubber cord whose electrical resistance changes as the cord is stretched (FIG. 44B, 45B).

17. A warning device for an IV bag dispensing medication or blood to detect when contents of the bag fall below a predetermined level without requiring the bag or a section thereof to stretch, the warning device comprising:

a. a sensor composed of a stretchable material that changes either resistance, capacitance, or inductance as stretch of the sensor changes (FIGS. 44, 45);

b. the sensor configured to be attached to a flaccid foldable collapsible bag filled with liquid medication or blood, with at least a portion of the bag being covered by, and free to move relative to at least a portion of the sensor (FIGS. 43, 44);

c. the sensor being attached to the bag so that either:

i. the sensor wraps around an entire perimeter of the bag, but with a perimeter of the sensor being smaller than the perimeter of the bag, requiring either:'

A. the bag is folded and collapsed to fit within the smaller perimeter of the sensor when the sensor is unstretched, or B. the sensor is stretched to fit around and cover the entire perimeter of the bag causing at least a portion of the bag to fold or collapse underneath the stretched sensor (FIGS. 45A, 46A, 47A); or ii. the sensor covers a portion of the bag perimeter, such that when the bag is empty; the sensor is unstretched and the portion of the bag perimeter covered by the unstretched sensor has a linear material length longer than the length of the unstretched sensor, requiring;

A. the bag is collapsed and folded to fit within the space covered by the sensor in its unstretched state, B. the sensor is stretched to cover a portion of the bag causing the bag to be folded or collapsed underneath the stretched sensor:

d. so that when the contents in the bag exceed a predetermined level it stretches the sensor and when the contents falls below a predetermined level it no longer stretches the sensor (FIGS. 46B, 46C, 47B, 47C), the sensor also configured to be located on the bag at a predetermined position relative to a predetermined level of medication or blood in the bag to insure that the bag pushes into and exerts force onto the sensor without requiring the bag or a section thereof to stretch (FIG. 44B);

e. in response to such a force, the sensor changes its shape by decreasing an amount of stretch (FIG. 44B), which changes the sensor's resistance, capacitance, or inductance;

f. and further such that when the level of medication or blood within the bag drops below a predetermined level, indicating that the sensor is no longer sufficiently stretched, thereby changing its resistance, capacitance, or inductance to indicate this condition (FIG. 45B);

g. an electronic module configured to be connected to the sensor, to detect the resistance, capacitance or inductance value that corresponds to the sensor no longer being sufficiently stretched, and to generate a warning signal that the bag is below the predetermined level (FIG. 48);

h. the warning signal being fed to at least one of a warning indicator such as a vibration, audible or visual device, a Bluetooth transmitter, a Wi-Fi transmitter, or a warning cable for connection to a remote device, or combinations thereof (FIG. 48).

18. The warning device of claim 17 wherein at least one of the vibration, audible or visual device, Wi-Fi transmitter, or Bluetooth transmitter is worn by a person to whom the bag is attached to indicate when the level of medication or blood in the bag has fallen below the predetermined level or when the bag is almost empty and may need to be replaced.

19. The warning device of claim 17 wherein at least one of the warning cable, the Wi-Fi transmitter, or the Bluetooth transmitter is connected to a remote device located at a attendant's station to indicate when the level of medication or blood in the bag has fallen below the predetermined level or when the bag is almost empty and may need to be replaced.

20. The warning device of claim 17 wherein the sensor is a stretchable carbon impregnated rubber cord whose electrical resistance changes as the cord is stretched (FIG. 16A, 44B).

* * * * *